United States Patent [19]

McCall

[11] 4,159,331
[45] Jun. 26, 1979

[54] ANTIHYPERTENSIVE 4-AMINOQUINOLINES

[75] Inventor: John M. McCall, Kalamazoo, Mich.
[73] Assignee: The Upjohn Company, Kalamazoo, Mich.
[21] Appl. No.: 903,200
[22] Filed: May 5, 1978
[51] Int. Cl.² ............... A61K 31/505; C07D 401/00
[52] U.S. Cl. ................................. 424/251; 424/250; 424/249; 544/182; 544/212; 544/295; 544/357; 544/363
[58] Field of Search .................. 544/363, 295, 357; 424/250, 251, 249

[56] References Cited

U.S. PATENT DOCUMENTS

| 3,362,956 | 1/1968 | Archer | 544/398 |
|---|---|---|---|
| 3,992,382 | 11/1976 | Coverdale et al. | 544/363 |

FOREIGN PATENT DOCUMENTS 2229413 12/1974 France.

Primary Examiner—Paul M. Coughlan, Jr.
Attorney, Agent, or Firm—Hans L. Berneis; Robert A. Armitage

[57] ABSTRACT

Antihypertensive compounds for the treatment of hypertensive mammals, including man, of the formula III:

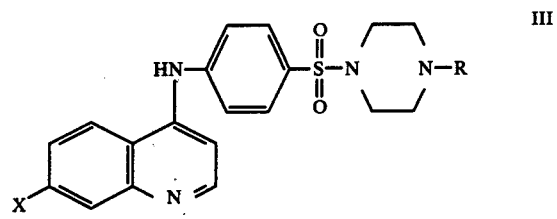

wherein X is chloro or trifluoromethyl; wherein R is a radical such as triazinyl, pyrazinyl, pyridinyl, pyrimidinyl, phenyl, or the above radicals substituted by one or two trifluoromethyl, halo, alkyl, alkoxy, dialkylamino or alkylthio groups; or R is the group

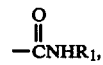

in which $R_1$ is phenyl, phenyl substituted with one or two halo atoms, alkoxy or alkyl groups, trifluoromethyl, or $R_1$ is alkylphenylsulfonyl; or R is the group —$SO_2R_2$, in which $R_2$ is dialkylamino, phenyl, phenyl substituted with halo atoms, alkyl, or alkoxy groups, or trifluoromethyl are prepared from (7-chloro)- or (7-trifluoromethyl)-4-chloroquinoline or 1-[[4-[[(7-chloro)- or (7-trifluoromethyl)quinolinyl]amino]phenyl]sulfonyl]piperazine.

13 Claims, No Drawings

ANTIHYPERTENSIVE 4-AMINOQUINOLINES

BRIEF SUMMARY OF THE INVENTION
FIELD OF THE INVENTION

This invention concerns new organic compounds; in particular, [1-substituted-4-(quinolinylaminophenyl)sulfonyl]piperazines III, their use as antihypertensives, and their formulations. Compound III is of the formula:

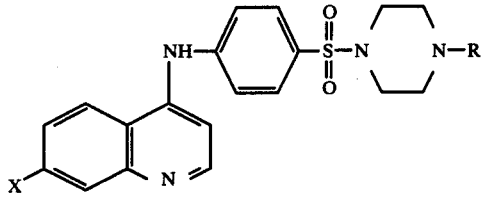

III wherein X is chloro or trifluoromethyl; wherein R is a radical selected from the group consisting of triazinyl, pyrazinyl, pyridinyl, pyrimidinyl, phenyl, or the above radicals substituted by one or two trifluoromethyl, alkyl, halo, alkoxy, dialkylamino, or alkylthio groups, or in the case of pyridine, by 1 to 4 hydrogen atoms, or combinations of substituents, in which alkyl and alkoxy are each of 1 to 3 carbon atoms, inclusive, and halo is fluoro, bromo or chloro; or R is the group

in which $R_1$ is phenyl, phenyl substituted with one or two halo, alkoxy, or alkyl groups, trifluoromethyl, or $R_1$ is alkylphenylsulfonyl, in which alkyl, alkoxy, and halo are defined as above; or R is the group —$SO_2R_2$, in which $R_2$ is dialkylamino, phenyl, phenyl substituted with one or two halo, alkyl or alkoxy groups, or trifluoromethyl, in which alkyl, alkoxy and halo are defined as hereinabove.

The new compounds and the processes of this invention can be illustratively represented by the following schemes:

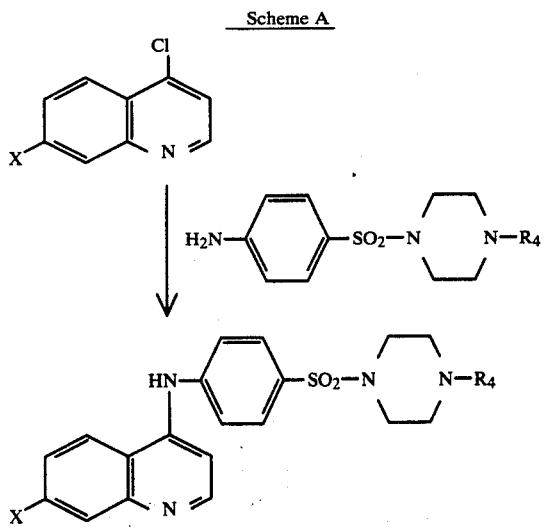

wherein X is defined above and $R_4$ is phenyl or substituted phenyl as defined in R above, or 2-pyridinyl, or

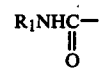

or—$SO_2R_2$ as defined above.

Scheme B

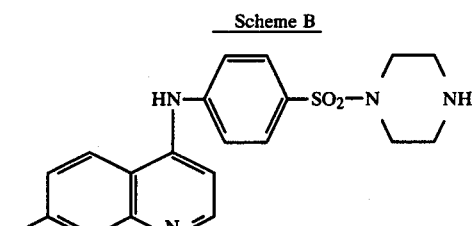

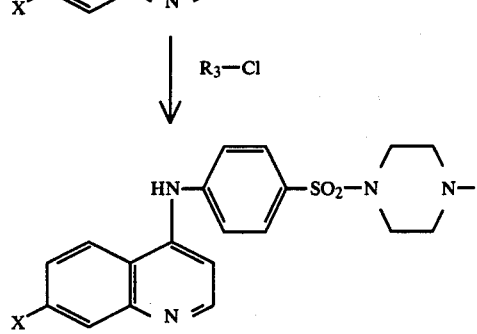

wherein $R_3$ is a substituted or unsubstituted pyrazinyl, pyrimidinyl, triazinyl, or pyridinyl, as defined for R above, or—$SO_2R_2$ as defined above.

Scheme C

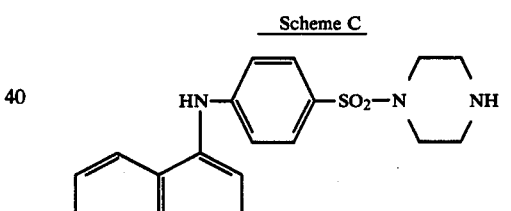

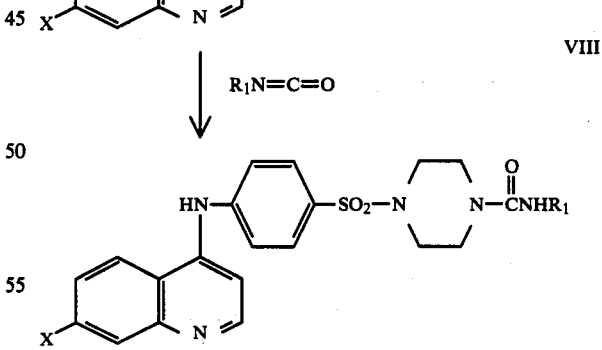

wherein $R_1$ and X are as defined above.

The reagent II can be produced in the following manner, as is also described in the Examples.

Scheme D

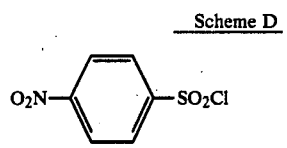

-continued

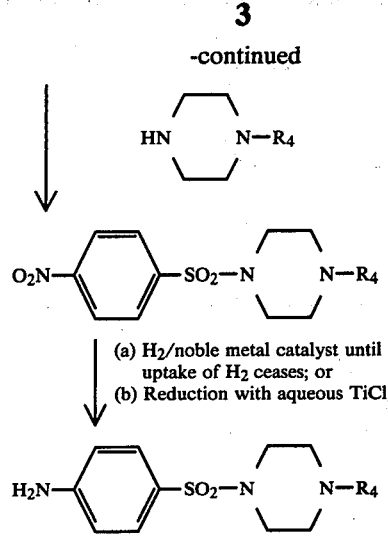

wherein R₄ is phenyl or substituted phenyl as defined for R above, or 2-pyridinyl, or SO₂R₂ or

as defined above.

The starting monosubstituted piperazines (formula X) are either commercially available or can be prepared from readily available starting materials by methods known in the art; see, for example, Polland et al, J. Amer. Chem. Soc., 76, 1853(1954).

Those compounds of formula X wherein R is

or—SO₂R₂ can be prepared by reaction of piperazine with one equivalent of the desired isocyanate (R₁N=C=O) in a nonpolar solvent such as methylene chloride or the desired sufonyl or sulfamoyl halide, respectively, in an inert solvent in the presence of an acid scavenger such as triethylamine.

In the reduction (from XI to II) in Scheme D-method (a) the carbonyl function of the urea (formula XI wherein R₄ is

is reduced more slowly than the nitro functionality on the phenyl ring; thus selective reduction can be attained. Reduction method (b) proceeds effectively regardless of R₄, and is preferred when the substituents on R₄ are known to interfere with the catalytic reduction (e.g., halo, alkylthio).

The preferred processes for the preparation of compounds wherein R is substituted or unsubstituted pyrazinyl, triazinyl, pyrimidinyl, pyridinyl,—SO₂R₂, or—CONHR₁ are shown in Schemes B and C.

The preparation of starting compound V can be accomplished as shown in Scheme E:

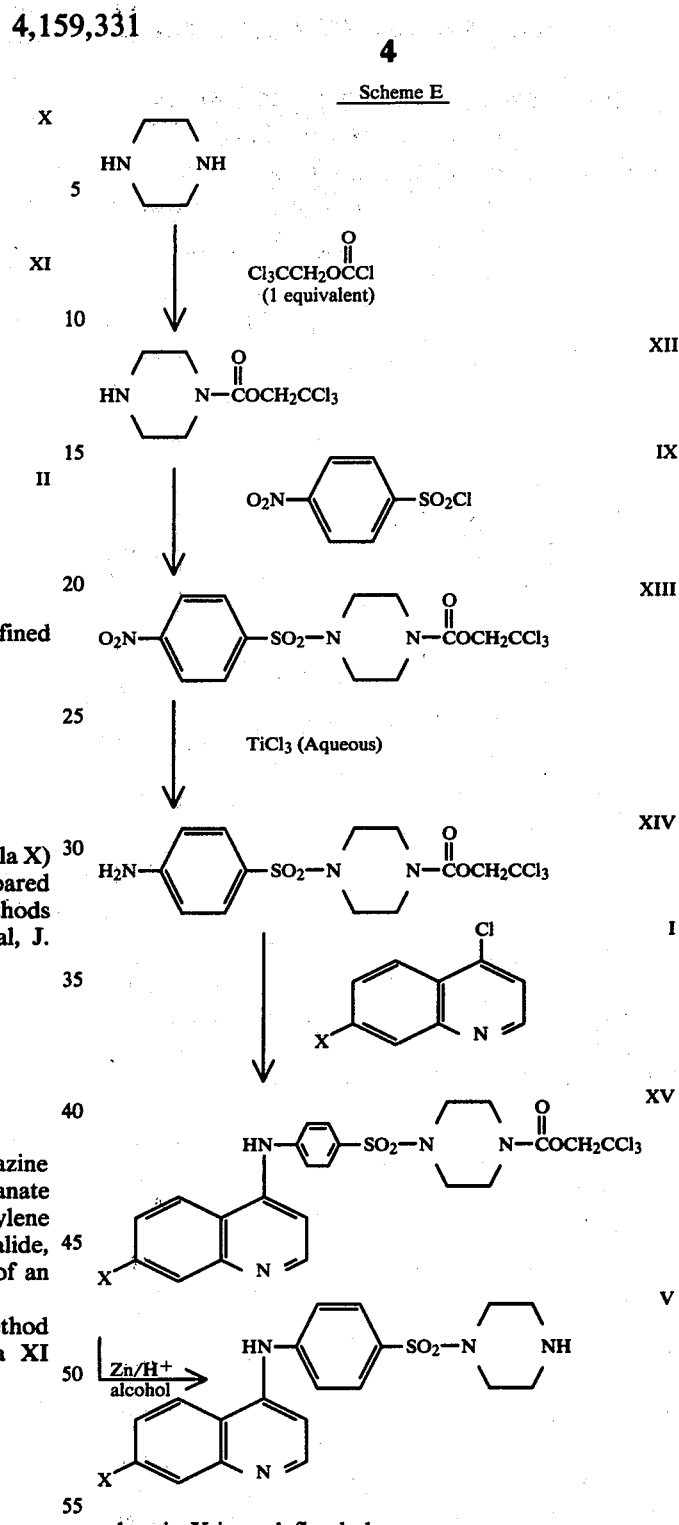

wherein X is as defined above.

The starting compounds 1 of this invention are commercially available or can be prepared as described in U.S. Pat. No. 3,632,761.

The invention also embraces the pharmacologically acceptable acid addition salts of compounds of formula III and pharmaceutical formulations of compounds of formula III or salts thereof.

The following art was considered by the inventor:

U.S. Pat. No. 3,933,829; British Patent specification No. 1,445,595; and French Pat. No. 2,229,413.

The first two patents disclose a heterocyclic moiety on the sulfonyl group which contains only one nitrogen as a ring member, i.e., piperidine, and substituted piperidine. The French patent discloses substituent moieties on piperazine such as hydrogen, alkyl, benzyl, clearly not the moieties disclosed and claimed by the inventor in the definition of R in formula III described above.

PREFERRED EMBODIMENT OF THE INVENTION

The alkyl groups in this invention, having 1 to 3 carbon atoms, inclusive, comprise methyl, ethyl, propyl, and isopropyl, with methyl preferred.

The alkoxy groups having 1 to 3 carbon atoms, inclusive, comprise methoxy, ethoxy, propoxy and isopropoxy.

The preferred halogens are chloro and fluoro.

A preferred group of compounds of this invention are of formula IIIA

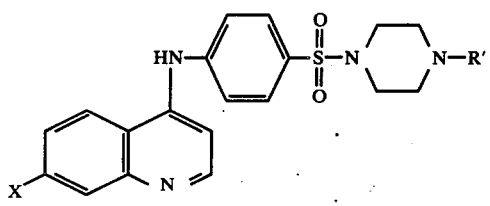

wherein X is chloro or trifluoromethyl; wherein R' is a radical selected from the group consisting of pyridinyl, pyrmidinyl, or phenyl, or the above radicals substituted by one or two trifluoromethyl, alkyl, alkoxy, or halo groups, or in the case of pyridine, by 1 to 4 halogen atoms, or combinations of substituents, in which alkyl and alkoxy are each of 1 to 3 carbon atoms, inclusive, and halo is fluoro or chloro; or R' is the group $SO_2R_2$, in which $R_2$ is dialkylamino, phenyl substituted with one or two halo, alkyl, or alkoxy, or trifluoromethyl groups, in which alkyl, alkoxy and halo are defined as hereinabove, or the pharmacologically acceptable salts thereof.

Another preferred group of compounds of this invention is of the formula IIIB

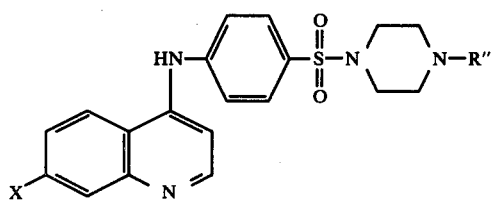

wherein X is chloro or trifluoromethyl; wherein R'' is a radical selected from the group consisting of pyridinyl, pyrimidinyl or phenyl, or the above radicals substituted by one or two trifluoromethyl, alkyl, alkoxy or halo groups, or, in case of pyridine, by 1 to 4 halogen atoms, or combinations of substituents, in which alkyl and alkoxy are each of 1 to 3 carbon atoms, inclusive, and halo is fluoro or chloro; or R'' is the group

—CNHR₁, in which $R_1$ is phenyl, phenyl substituted with one or two halogens, alkoxy, alkyl, or trifluoromethyl group, or $R_1$ is alkylphenylsulfonyl, in which alkyl, alkoxy, and halo are defined as above, or the pharmacologically acceptable acid addition salts thereof.

The most preferred compounds of this invention are of the formula 111C

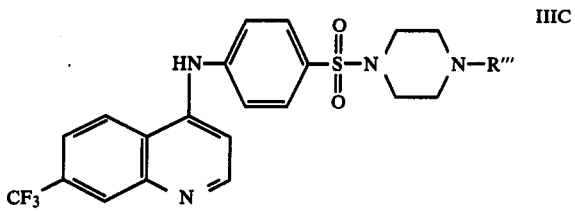

wherein R''' is a radical selected from the group consisting of pyridinyl, pyrimidinyl or phenyl, or the above radicals substituted by one or two trifluoromethyl, alkyl, alkoxy, or halo groups, in which alkyl and alkoxy are each of 1 to 3 carbon atoms, inclusive, and halo is fluoro or chloro; or the pharmacologically acceptable acid addition salts thereof.

The pharmacologically acceptable salts of compound of the formula III (including the preferred compounds of formulae IIIA, IIIB or IIIC) comprise the hydrochlorides, hydrobromides, hydriodides, sulfates, phosphates, cyclohexanesulfamates, pamoates, methanesulfonates, and the like, prepared by reacting a compound of formula III with the stoichiometrically calculated amount of the selected pharmacologically acceptable acid in a suitable solvent.

The compounds were tested for hypotensive activity and for cataractogenic activity.

The hypotensive activity of the new compounds was determined by measuring the mean-arterial blood pressure at different dosage levels in the rat and determining from it the means blood pressure reduction after 4 and 24 hours.

The mean arterial blood pressure is defined in the art as:

$$\frac{\text{systolic pressure} - \text{diastolic pressure}}{3} + \text{diastolic pressure}$$

Also, decrease of the heart rate at 4 and 24 hours after drug administration was determined.

The following is a brief description of the precedures and the basis of reporting compounds as active or inactive hypotensive agents in the assay.

Methods: Chronic abdominal aortic indwelling cannula are exteriorized at the nape of the neck of Upjohn Sprague Dawley specific pathogen-free female rats. Aortic blood pressure is monitored with a transducer-polygraph system. Mean arterial blood pressure is obtained by electrical integration of the phasic pressure. Heart rate is obtained by electronically counting arterial pulses. Two unanesthetized rats are each treated orally with single 50 mg/kg doses of the test compound. Test agents are suspended in Upjohn Vehicle 98 [each ml of vehicle contains carboxymethylcellulose (10 mg), polysorbate 80 (4 mg) and polyparaben (0.42 mg) in water ] or an appropriate carrier. Injection volume is 10 cc/kg. Mean arterial blood pressure and heart rate are observed before, and 4 and 24 hours after drug administration.

Results: Blood pressures of two rats are averaged before, and 4 and 24 hours after oral treatment with the test compound. If the change, initial vs 4 and/or 24 hours, is <5 mm Hg, the compound is considered inactive. Compounds that produce average increases in blood pressure of >5 mm Hg are reported as possible pressors. If the average change is a decrease of <5 mm Hg, the test is repeated. Average change is then calculated for two rats. If the decrease is >5 mm Hg, the compound is considered to be an active hypotensive agent.

Heart rates are also obtained before, and 4 and 24 hours after drug administration. If the average change, initial vs 4 and/or 24 hours, is <65 beats per minute, the compound is not considered to have altered the heart rate. If the average change is >65 beats per minute, the compound is considered to have altered the heart rate. An in vitro test was found to test for the cataractogenic activity of compounds. A description of this method can be found in Edwards, et al, Experimental Eye Research, 10, 228(1970), and is as follows:

MATERIALS AND METHODS

Under sterile conditions, the commercial *Grand Island Biologicals Co. Medium #199* containing phenol red at a concentration of 0.002% was diluted 1:10 with sterile distilled water. The dilute Medium #199 was then supplemented with foetal calf serum (10%, v/v), 100 units/ml of penicillin, and 100 mg/ml of streptomycin. The final pH of this growth medium was adjusted with sterile 0.5 N sodium hydroxide.

Compounds to be tested were dissolved or suspended at a concentration of 15 mM (15 millimolar) in Vehicle 124 (0.25% methylcellulose in isotonic saline) containing 10% dilute Medium #199. When necessary, pH adjustments were made to maintain the pH at 7.2.

Eyes were removed from 11—13 day chick embryos in a sterile surface hood. All subsequent steps employed sterile techniques. Lenses were removed and freed of adhering humor. Each lens was then placed into a sterile 12×75 mm test tube containing the incubation medium described above. After all lenses were removed, an aliquot (10–100 μl) of Vehicle 124 containing Medium #199 with or without the test compound was added to a final volume of 300 μl. Paired lenses were incubated with different drugs. Each tube was stoppered with gauze-wrapped paper plugs and incubated at 36° C. Lenses were incubated for four hours after which the incubation medium containing the drug was removed by aspiration. Lenses were rinsed once with growth medium and that medium removed; 300 μl of fresh growth medium free of drug was added to the lens and the incubation was continued at 36° C. The pH changes in the growth media were determined semi-quantitatively by color comparison of the tube with a set of standard solutions prepared over the range of pH 4 to 8 and containing the same concentration of phenol red as in the growth medium.

comparison between pH 4 to 8 of prepared standard solutions any degree of cataractogenic activity is discovered. The compounds of this invention did not inhibit respiration (metabolism).

This invention relates also to pharmaceutical dosage unit forms for systemic administration (oral and parenteral administration) of compounds of formula III in obtaining unexpectedly advantageous beneficial results in hypertensive conditions in mammals (including humans and valuable warm-blooded animals such as dogs, cats, and other domestic animals). The term "dosage unit form" as used in this specification and in the claims refers to physically discrete units suitable as unitary dosages for mammalian subjects, each unit containing a predetermined quantity of the essential active ingredient calculated to produce the desired effect in combination with the required pharmaceutical means which adapt the said ingredient for systemic administration. The specification for the novel dosage unit forms of this invention are dictated by and directly dependent on the unique characteristics of the essential active ingredient and the particular effect to be achieved in view of the limitations inherent in the art of compounding such as essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids; for example, starch, sucrose, kaolin, dicalcium phosphate, gelatin, acacia, corn starch, talc, and the like. Capsules, both hard and soft, are formulated with suitable diluents and excipients; for example, edible oils, talc, calcium carbonate, and the like, and also, calcium stearate. Liquid preparations for oral administration are prepared in water or aqueous solutions which advantageously contain suspending agents; for example, sodium carboxymethylcellulose, methylcellulose, acacia, polyvinyl pyrrolidone, polyvinyl alcohol and the like. In the case of injectable forms, they must be sterile and must be fluid to the extent that easy syringeability exists. Such preparations must be stable under the conditions of manufacture and storage, and ordinarily contain, in addition to the basic solvent or suspending liquid, preservatives in the nature of bactericidal and fungicidal agents; for example, parabens, chlorobutanol, benzyl alcohol phenol, and the like. In many cases it is prefera-

| Color | Purple | Pink | Slightly Pink | Slightly Orange | Orange | Gold | Light Gold | Yellow |
|---|---|---|---|---|---|---|---|---|
| pH | 8 | 7.2-7.4 | 6.5 | 6 | 5.5 | 5 | 4.5 | 4.0 |

Color comparisons were made after 17–19 hours, 24 hours, and 48 hours. In some experiments comparisons were also made at longer intervals.

As a result of the metabolism by the lenses during incubation, principally due to lactic acid formation, a decrease of the pH and change of color of the indicator from pink to yellow is observed. Thus, by colormetric ble to include isotonic agents; for example, sugars or sodium chloride. Carriers and vehicles include vegetable oils, ethanol, polyols; for example, glycerol, propylene glycol, liquid polyethylene glycol, and the like. Any solid preparations for subsequent extemporaneous preparation of sterile injectable preparations are sterilized, preferably by exposure to a sterilizing gas; for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 5 to about 100 mg of the essential active ingredient per dosage unit form, which, as aforesaid, may be in the form of a solid oral preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain antihypertensive effects within the effective nontoxic range. Expressed otherwise, an amount of the essential acitve ingredient is provided to a recipient within a range from about 0.05 mg per kg to about 20 mg per kg of body weight of the recipient, preferably 0.1 to 10 mg per kg; the most preferred dose range is 0.2 to 5 mg per kg.

The amount administered depends on the age, weight, and condition of the patient as determined by the physician.

The following examples are illustrative of the products and processes of the present invention but are not to be construed as limiting.

EXAMPLE 1

1-(4-fluorophenyl)-4-[[4-[[7-(trifluoromethyl)-4-quinolinyl]amino]phenyl]sulfonyl]piperazine

A.

1-[(p-nitrophenyl)sulfonyl]-4-(p-fluorophenyl)piperazine

A mixture of 7.50 g (0.0338 m) of p-nitrobenzenesulfonyl chloride, 6.10 g (0.00338 m) of p-fluorophenylpiperazine, 4.72 ml (0.0338 m) of triethylamine, and 200 ml of tetrahydrofuran is stirred at reflux for one hour, then allowed to stir at room temperature overnight. The tetrahydrofuran is then removed in vacuo and the residue is extracted with methylene chloride and the organic layer is washed with aqueous sodium hydroxide followed by brine. The organic layer is filtered through anhydrous sodium sulfate and taken to dryness. Crystallization from methylene chloride/Skellysolve ® B hexanes gave 10.71 g (87%) of 1-[(p-nitrophenyl)sulfonyl]-4-(p-fluorophenyl)piperazine of melting point 189°–191° C.

B.

1-[(p-aminophenyl)sulfonyl]-4-(p-fluorophenyl)piperazine

A mixture of 5.00 g (0.0137 m) of 1-[(p-nitrophenyl)sulfonyl]-4-(p-fluorophenyl)piperazine, 0.2 g of platinum oxide, and 150 ml of chloroform is shaken under hydrogen on a Parr hydrogenation apparatus for one hour. The mixture is then filtered through a sintered glass funnel containing activated carbon and sand to remove the catalyst. The filtrate is concentrated in vacuo and then extracted with methylene chloride/aqueous sodium bicarbonate. The organic layer is filtered through anhydrous sodium sulfate and taken to dryness. The residue is crystallized from methanol to give 2.16 g of 1-[(p-aminophenyl)sulfonyl]-4-(p-fluorophenyl)piperazine containing a minor impurity. Recrystallization from methanol gives an analytical sample with a melting point of 180.5°–181.5° C.

Anal. calcd. for $C_{16}H_{18}FN_3O_2S$: Calcd.: C, 57.29; H, 5.41; N, 12.53. Found: C, 57.34; H, 5.56; N, 12.47.

C.

1-(4-fluorophenyl)-4-[[4-[[7-(trifluoromethyl)-4-quinolinyl]amino]phenyl]sulfonyl]-piperazine To 2.15 g (0.00641 m) of 1-[(p-aminophenyl)sulfonyl]-4-(p-fluorophenyl)piperazine in 150 ml of ethanol is added 0.46 ml (0.00641 m) of acetyl chloride in ethanol. The mixture is stirred for 10 minutes, after which 2.10 g (0.00641 m) of 4-chloro-7-trifluoromethylquinoline is added. The mixture is heated at reflux for 3 hours and then at room temperature overnight. The ethanol is then removed and the residue is shaken with methylene chloride and aqueous sodium bicarbonate. The resulting solid is collected and triturated with methanol to give 0.40 g of 1-(4-fluorophenyl)-4-[[4-[[7-(trifluoromethyl)-[4-quinolinyl]amino]phenyl]sulfonyl]piperazine of melting point 246.5°–148.5° C.

EXAMPLE 2

1-(2-methoxyphenyl)-4-[[4-[[7-trifluoromethyl)-4-quonolinyl]amino]phenyl]sulfonyl]piperazine

A.

1-[(p-nitrophenyl)sulfonyl]-4-(o-methoxyphenyl)piperazine

To a mixture of 7.50 g (0.0338 m) of p-nitrobenzenesulfonylchloride, 4.72 ml (0.0338 m) of triethylamine, and 200 ml of tetrahydrofuran is added in small aliquots 6.84 g (0.0338 m) of o-methoxyphenylpiperazine. An ice bath is added as the exotherm begins and approximately 100 ml of methylene chloride is added to facilitate stirring.

After stirring at room temperature over the weekend, the solvent is removed in vacuo and the residue is extracted with methylene chloride, then 1N aqueous sodium hydroxide, followed by brine. The organic layer is filtered through anhydrous sodium sulfate and taken to dryness. The product (11.32 g, 89%) is crystallized from methylene chloride/Skelly-solve ® B hexanes to give 1-[(p-nitrophenyl)sulfonyl]-4-(2-methoxyphenyl)piperazine of melting point 202°–204° C.

B.

1-[(p-aminophenyl)sulfonyl]-4-(o-methoxyphenyl)piperazine

A mixture of 5.00 g (0.0133 m) of 1-[(p-nitrophenyl)-sulfonyl]-4-(o-methoxyphenyl)piperazine, 0.28 g of platinum oxide and 150 ml of chloroform is shaken under pressure in a Parr hydrogenator. After hydrogen ceases to be taken up (1 hour), the reaction mixture is filtered through a fine sintered glass funnel. The filtrate is taken to dryness and crystallized once from methanol/methylene chloride and a second time from methanol to give 1.9 g (41%) of 1-[(p-aminophenyl)sulfonyl]-4-(o-methoxyphenyl)-piperazine of melting point 230°–232° C.

C.

1-(2-methoxyphenyl)-4-[[4-[[7-(trifluoromethyl)-4-quinolinyl]amino]phenyl]sulfonyl]piperazine To 1.73 g (0.00498 n) of 1-[(p-aminophenyl)sulfonyl]-4-(o-methoxyphenyl)piperazine in absolute ethanol is added 0.35 ml acetyl chloride in 5 ml ethanol (source of hydrogen chloride). After stirring for 5 minutes, 1.15 g (0.00498 m) of 4-chloro-7-trifluoromethylquinoline is added. The reaction mixture is stirred at reflux for 3 hours and at room temperature overnight. The solvent is then removed in vacuo and the residue is extracted with methylene chloride/aqueous sodium bicarbonate. The organic layer is filtered through anhydrous sodium sulfate and taken to dryness and the product mixture is chromatographed on silica gel, once with 4% methanol: 96% methylene chloride as eluant, and a second time with methylene chloride as the eluant. Crystallization from methylene chloride/Skelly-solve ® B hexanes gives 1.61 g (61%) of 1-(2-methoxyphenyl)-4-[[4-[[7-(trifluoromethyl)-4-quinolinyl]amino]phenyl]sulfonyl]piperazine of melting point 146°–148° C.

Anal. calcd. for $C_{27}H_{25}F_3N_4O_3S$: C, 59.77; H, 4.64; N, 10.33. Found: C, 59.76; H, 4.91; N, 9.90.

EXAMPLE 3

1-(2-methylphenyl)-4-[[4-[[7-(trifluoromethyl)-4-quinolinyl]amino]phenyl]sulfonyl]piperazine and its mono-hydrate

A.

1-[(p-nitrophenyl)sulfonyl]-4-(o-methylphenyl)piperazine

A mixture of 7.88 g (0.0356 m) of p-nitrobenzenesulfonylchloride, 6.27 g (0.0356 m) of 1-(o-tolyl)piperazine, 4.96 ml (0.0356 m) of triethylamine, and 100 ml of tetrahydrofuran is stirred at room temperature for 18 hours. The solvent is then removed in vacuo and the residue is extracted with methylene chloride/aqueous sodium bicarbonate and brine. The organic layer is filtered through sodium sulfate and taken to dryness. Crystallization from methylene chloride/Skellysolve ® B hexanes gives 9.51 g of 1-[(p-nitrophenyl)sulfonyl]-4-(o-methylphenyl)piperazine of melting point 176°–177.5° C. and 1.33 g of a second crop (84%).

B.

1-[(p-aminophenyl)sulfonyl]-4-(o-methylphenyl)piperazine

A mixture of 5.00 g (0.0142 m) of 1-[(p-nitrophenyl)-sulfonyl]-4-(o-methylphenyl)piperazine, 0.3 g of platinum oxide, and 150 ml of chloroform is shaken under pressure on a Parr hydrogenator until hydrogen uptake ceases (25 minutes). The catalyst is removed on a fine sintered glass funnel and the filtrate is taken to dryness. Crystallization from ethyl acetate/methylene chloride/Skellysolve ® B hexanes gives 2.66 g (57%) of 1-[(p-aminophenyl)-sulfonyl]-4-(o-methylphenyl)piperazine.

C.

1-(2-methylphenyl)-4-[[-4-[[7-(trifluoromethyl)-4-quinolinyl]amino]phenyl]sulfonyl]piperazine hydrate To 2.00 g (6.03 mm) of 1-[(p-aminophenyl)-sulfonyl]-4-(o-methylphenyl)piperazine in absolute ethanol is added 0.43 ml acetyl chloride in ethanol (source of hydrogen chloride). After stirring for 10 minutes, 1.40 g (6.03 mm) of 4-chloro-7-trifluoromethylquinoline is added and the reaction mixture is stirred at reflux for 2½ hours and then overnight at room temperature. The solvent is then removed in vacuo and the residue is extracted with methylene chloride and aqueous sodium bicarbonate. The organic layer is filtered through anhydrous sodium sulfate and taken to dryness. Crystallization twice from methylene chloride/Skellysolve ® B hexanes gives 1.67 g (51%) of 1-(2-methylphenyl)-4-[[4-[[7-(trifluoromethyl)-4-qinolinyl]amino]phenyl]sulfonyl]piperazine of melting point 140°–145° C., which is analyzed as a monohydrate.

Anal. calcd. for $C_{27}H_{25}F_3N_4O_2S.H_2O$: Calcd.: C, 59.55; H, 5.00; N, 10.29. Found: C, 59.94; H, 4.79; N, 10.35.

Heating the monohydrate at 70°–90° C. for 24–36 hours at a reduced pressure gives the free base.

EXAMPLE 4

1-(2-pyridinyl)-4-[[4-[[7-(trifluoromethyl)-4-quinolinyl]amino]phenyl]sulfonyl]piperazine

A. 1-[(p-nitrophenyl)sulfonyl]-4-(2-pyridinyl)piperazine

To a mixture of 6.42 g (0.03736 m) of 1-(2-pyridinyl)-piperazine, 5.21 ml (0.03736 m) of triethylamine, and 250 ml of tetrahydrofuran is added 8.28 g (0.03736 m) of p-nitrobenzenesulfonyl chloride. The mixture is stirred at room temperature for 1⅜ hours, after which it is concentrated in vacuo. The residue is then extracted with methylene chloride and aqueous sodium bicarbonate and the organic layer is taken to dryness to give 10.62 g (82%) of 1-[(p-nitrophenyl)sulfonyl]-(2-pyridinyl)piperazine.

B.

1-[(p-aminophenyl)sulfonyl]-4-(2-pyridinyl)piperazine

A mixture of 10.62 g (0.0305 m) of 1-[(p-nitrophenyl)-sulfonyl]-4-(2-pyridinyl)piperazine, 1.5 g of 5% palladium on charcoal, and 150 ml of absolute ethanol is shaken under hydrogen on a Parr hydrogenator. After the theoretical amount of hydrogen has been taken up, the catalyst is filtered off and the filtrate is taken to dryness. The product, 1-[(p-aminophenyl)sulfonyl]-4-(2-pyridinyl)piperazine, is crystallized from methanol/methylene chloride to give 7.89 g (81%) of 1-[(p-aminophenyl)sulfonyl]-4-(2-pyridinyl)piperazine of melting point 208°–210° C.

C.

1-(2-pyridinyl)-4-[[4-[[7-(trifluoromethyl)-4-quinolinyl]amino]phenyl]sulfonyl]piperazine To 6.40 g (0.02 m) of 1-[p-aminophenyl)-sulfonyl]-4-(2-pyridinyl)piperazine in 130 ml of absolute ethanol is added 1.67 ml of concentrated hydrochloric acid. After stirring for 10 minutes, 4.65 g (0.02 m) of 4-chloro-7-trifluoromethylquinoline is added. The mixture is heated at reflux for 4 hours and then cooled. The reaction mixture is then concentrated in vacuo and the residue shaken with methylene chloride and 1N aqueous sodium hydroxide. The solids are filtered off and the filtrate is extracted with methylene chloride/1N aqueous sodium hydroxide. The organic layer is taken to dryness and chromatographed on silica gel using 3% methanol:97% methylene chloride as eluant. The product is crystallized from methylene chloride/Skellysolve ® B hexanes to give 7.4 g (72%) of 1-(2-pyridinyl)-4-[[4-[[7-(trifluoromethyl)-4-quinolinyl]amino]phenyl]sulfonyl]piperazine of melting point 201.5°–203° C.

Calcd. for $C_{25}H_{22}F_3N_5O_2S$: Calcd.: C, 58.47; H, 4.32; N, 13.62. Found: C, 58.25; H, 4.24; N, 13.60.

EXAMPLE 5

1-(m-chlorophenyl)-4-[[4-[[7-(trifluoromethyl)-4-quinolinyl]amino]phenyl]sulfonyl]piperazine

A.
1-[(p-nitrophenyl)sulfonyl]-4-(m-chlorophenyl)piperazine

In the manner given in Example 1A, p-nitrobenzenesulfonyl chloride, 1-(m-chlorophenyl)piperazine, and triethylamine are stirred at reflux to give 1-[(p-nitrophenyl)sulfonyl]-4-(m-chlorophenyl)piperazine.

B.
1-[(p-aminophenyl)sulfonyl]-4-(m-chlorophenyl)piperazine

1-[(p-Nitrophenyl)sulfonyl]-4-(m-chlorophenyl)piperazine is reduced with aqueous titanium trichloride in ether solution by dropwise addition of aqueous TiCl3 until the purple color is no longer discharged. The reaction progress is followed by thin layer chromatography. Work-up with concentrated ammonium hydroxide and subsequently aqueous potassium hydroxide followed by isolation, drying, and concentration of the organic layer gives 1-[p-aminophenyl)sulfonyl]-4-(m-chlorophenyl)piperazine.

C.
1(m-chlorophenyl)-4-[[4-[[7-(trifluoromethyl)-4-quinolinyl]amino]phenyl]sulfonyl]piperazine In the matter given in Example 1C, 4-chloro-7-(trifluoromethyl)quinoline is heated with 1-[(p-aminophenyl)sulfonyl]-4-(m-chlorophenyl)piperazine to give 1-(m-chlorophenyl)-4-[[4-[[7-(trifluoromethyl)4-quinolinyl]amino]phenyl]sulfonyl]piperazine.

EXAMPLE 6

1-(o-Bromophenyl)-4-[[4-[[7-chloro-4-quinolinyl-]amino]phenyl]sulfonyl]piperazine

A.
1-[(p-nitrophenyl)sulfonyl]1-4-(o-bromophenyl)piperazine

In the manner given in Example 1A, p-nitrobenzenesulfonyl chloride, 1-(o-bromophenyl)piperazine and triethylamine are stirred at reflux to give 1-[(p-nitrophenyl)sulfonyl]-4-(o-bromophenyl)piperazine.

B.
1-[(p-aminophenyl)sulfonyl]-4-(o-bromophenyl)piperazine

In the manner given in Example 5B, 1-[(p-nitrophenyl)sulfonyl]-4-(o-bromophenyl)piperazine is reduced with titanium chloride (TiCl3) to give 1-[(p-aminophenyl)sulfonyl]-4-(o-bromophenyl)piperazine.

C.
1-(o-bromophenyl)-4-[[4-[[7-chloro-4-quinolinyl-]amino]phenyl]sulfonyl]piperazine In the manner given in Example 1C, 4,7-dichloroquinoline is heated with 1-[(p-aminophenyl)-sulfonyl]-4-(o-bromophenyl)piperazine to give 1-(o-bromophenyl)-4-[[4-[[7-chloro-4-quinolinyl]-amino]-phenyl]sulfonyl]piperazine.

EXAMPLE 7

1-(2,6-difluorophenyl)-4-[[4-[[7-chloro-4-quinolinyl-]amino]phenyl]sulfonyl]piperazine

A.
1-[(p-nitrophenyl)sulfonyl]-4-(2,6-difluorophenyl)piperazine

In the manner given in Example 1A, p-nitrobenzenesulfonyl chloride, 1-(2,6-difluorophenyl)piperazine and triethylamine are stirred at reflux to give 1(p-nitrophenyl)sulfonyl]-4-(2,6-difluorophenyl)piperazine.

B. 1-[(p-aminophenyl)sulfonyl]-4-piperazine

In the manner given in Example 5B, 1-[(p-nitrophenyl)sulfonyl]-4-(2,6-difluorophenyl)piperazine is reduced with titanium trichloride to give 1-[(p-aminophenyl)sulfonyl]-4-(2,6-difluorophenyl)piperazine.

C.
1-(2,6-difluorophenyl)-4-[[-chloro-4-quinolinyl]amino]-phenyl]sulfonyl]piperazine In the manner given in Example 1C, 4,7-dichloroquinoline is heated with 1-[(p-aminophenyl)-sulfonyl]-4-(2,6-difluorophenyl)piperazine to give 1-(2,6-difluorophenyl)-4-[[4-[[7-chloro-4-quinolinyl-]amino]phenyl]sulfonyl]piperazine.

EXAMPLE 8

1-(p-methylthiophenyl)-4-[[4-[[7-(trifluoromethyl)-4-quinolinyl]amino]phenyl]sulfonyl]-piperazine

A.
[1-[(p-nitrophenyl)sulfonyl]4-(p-methylthiophenyl)]piperazine

In the manner given in Example 2A, p-nitrobenzenesulfonyl chloride, 1-(p-methylthiophenyl)-piperazine and triethylamine are stirred at reflux to give 1-[(p-nitrophenyl)sulfonyl]-4-(p-methylthiophenyl)piperazine.

B.
[1-[(p-aminophenyl)sulfonyl]-4-(p-methylthiophenyl)-]piperazine

In the manner given in Example 5B, [1-(p-nitrophenyl)sulfonyl]-4-(p-methylthiophenyl)piperazine is reduced with TiCl3 to give [1-[(p-aminophenyl)sulfonyl]-4-(p-methylthiophenyl)]-piperazine.

C.
1-(p-methylthiophenyl)-4-[[4-[[7-(trifluoromethyl)-4-quinolinyl]amino]phenyl]-sulfonyl]-piperazine In the manner given in Example 2C, 4-chloro-7-trifluoromethylquinoline is heated with [1-[p-aminophenyl)sulfonyl]-4-methylthiophenyl]piperazine, to give 1-(p-methylthiophenyl)-4-[[4-[[7-(trifluoromethyl)-4-quinolinyl]amino]phenyl]sulfonyl]piperazine.

EXAMPLE 9

1-(2-Pyrimidinyl)-4-[[4-[[7-(trifluoromethyl)-4-quinolinyl]amino]phenyl]sulfonyl]piperazine

A.
1-(p-nitrophenylsulfonyl)-4-(2,2,2-trichloroethoxycarbonyl)piperazine

To a solution of 0.5 mol of piperazine and 0.5 mol of triethylamine in ether is added dropwise 0.25 mol of 2,2,2-trichloroethylchloroformate. The reaction mixture is stirred for 1–6 hours at room temperature (ca. 25° C.) and is then worked up with aqueous weak basic solution to give 1-(2,2,2-trichloroethoxycarbonyl)piperazine. This is reacted with p-nitrobenzenesulfonyl chloride in a non-polar solvent, e.g., tetrahydrofuran, to give 1-(p-nitrobenzenesulfonyl)-4-(2,2,2-trichloroethoxycarbonyl)piperazine.

B.

1-(p-aminophenylsulfonyl)-4-(2,2,2-trichloroethoxycarbonyl)piperazine

In the manner given in Example 5B, 1-(p-nitrophenylsulfonyl)-4-(2,2,2-trichloroethoxycarbonyl)- piperazine is reduced with TiCl₃ to give 1-(p-aminophenylsulfonyl)-4-(2,2,2-trichloroethoxycarbonyl)piperazine.

C.

1-[[4-[(7-trifluoromethyl-4-quinolinyl)-amino]phenyl]-sulfonyl]-4-(2,2,2-trichloroethoxycarbonyl)piperazine In the manner given in Example 4C, 1-(p-aminophenylsulfonyl)-4-(2,2,2-trichloroethoxycarbonyl)piperazine is heated with 4-chloro-7-trifluoromethylquinoline to give 1-[[4-[(7-trifluoromethyl-4-quinolinyl)amino]phenyl]-sulfonyl]-4(2,2,2-trichloroethoxycarbonyl)piperazine.

D.

1-[[4-[(7-trifluoromethyl-4-quinolinyl)-amino]phenyl]-sulfonyl]piperazine

Reaction of 1-[[4-[7-trifluoromethyl-4-quinolinyl)-amino]phenyl]sulfonyl]-4-(2,2,2-trichloroethoxycarbonyl)- piperazine with an excess of zinc dust in 5% acetic acid in an alcoholic solvent, e.g., methanol, at room temperature gives 1-[[4-[(7-trifluoromethyl-4-quinolinyl)amino]phenyl]sulfonyl]piperazine.

E.

1-(2-pyrimidinyl)-4-[[4-[(7-trifluoromethyl-4-quinolinyl)amino]phenyl]sulfonyl]piperazine A mixture of the product from Part D above, 2-chloropyrimidine, and triethylamine in a solvent such as ethylene glycol is heated at 75°–150° C. for 3 to 10 hours. The reaction mixture is cooled to room tempraturre and stirred at that temperature for another 10 to 20 hours, after which the mixture is worked up by standard procedures, e.g., aqueous sodium carbonate followed by methylene chloride extraction. 1-(2-Pyrimidinyl)-4-[[4-[(7-trifluoromethyl-4-quinolinyl)-amino]phenyl]sulfonyl]piperazine is isolated and purified by conventional methods.

Similarly, the corresponding 1-(2-pyrimidinyl)-4-[[4-[(7-chloro-4-quinolinyl)amino]phenyl]sulfonyl]piperazine can be prepared by using 4,7-dichloroquinoline in part C.

EXAMPLE 10

1-[3-(1,2,4-triazinyl)]-4-[[4[[7-chloro-4-quinolinyl-]amino]phenyl]sulfonyl]piperazine In the manner given in Example 9E, 3-chloro-1,2,4-triazine is heated with [[4-[(7-chloro-4-quinolinyl)amino]phenyl]sulfonyl]piperazine to give 1-[3-(1,2,4-triazinyl)]-4-[[4-[[7-chloro-4-quinolinyl]amino]phenyl]sulfonyl]piperazine.

EXAMPLE 11

1-[3-ethoxy-(2-pyrazinyl)]-4-[[4-[[7-(tri-fluoromethyl)-4-quinolinyl]amino]phenyl]sulfonyl]- piperazine In the manner given in Example 9E, 2-chloro-3-ethoxypyrazine in place of 2-chloropyrimidine, 1-[3-ethoxy-(2-pyrazinyl)]-4-[[4-[[7-(trifluoromethyl)-4-quinolinyl]amino]phenyl]-sulfonyl]piperazine is obtained.

EXAMPLE 12

1-[2,3,5,6-tetrachloro-(4-pyridinyl)]-4-[[4-[[7-chloro-4-quinolinyl]phenyl]sulfonyl]-piperazine In the manner given in Example 9E, but using pentachloropyridine in place of 2-chloropyrimidine and 4,7-dichloroquinoline in the place of 7-trifluoromethyl-4-chloroquinoline, 1-[2,3,5,6-tetrachloro-(4-pyridinyl)]-4-[[4[[7-chloro-4-quinolinyl]amino]-phenyl]sulfonyl]piperazine is obtained.

EXAMPLE 13

1-(dimethylaminosulfonyl)-4-[[4-[[7-(tri-fluoromethyl)-4-quinolinyl]amino]phenyl]sulfonyl]-piperazine To a mixture of [[4-[(7-trifluoromethyl-4-quinolinyl)amino]phenyl]sulfonyl]piperazine (prepared as in Example 9, part D) and triethylamine, in dimethyl formamide, is added dropwise an equimolar quantity of dimethylsulfamoyl chloride. The reaction mixture is stirred at room temperature for 15 to 25 hours and is then partitioned with methylene chloride-aqueous sodium carbonate. The organic phase is dried over sodium sulfate and is concentrated and purified by conventional methods to give 1-(dimethylaminosulfonyl)-4-[[4-[[7-(trifluoromethyl)-4-quinolinyl]amino]phenyl]sulfonyl]-piperazine.

EXAMPLE 14

1-[(4-chlorophenyl)sulfonyl]-4-[[4-[[7-chloro-4-quinolinyl]amino]phenyl]sulfonyl]piperazine In the manner given in Example 13 but using 4-chlorophenylsulfonyl chloride in place of sulfamoyl chloride, and [[4-[(7-chloro-4-quinolinyl)amino]-phenyl]sulfonyl]piperazine, 1-[(4-chlorophenyl)sulfonyl]-4-[[4-[[7-chloro-4-quinolinyl]amino]phenyl]sulfonyl]-piperazine is obtained.

EXAMPLE 15

1-[[o-(trifluoromethyl)phenyl]sulfonyl]-4-[[4-[[7-(trifluoromethyl)-4-quinolinyl]amino]-phenyl]sulfonyl]piperazine In the manner given in Example 13 but using o-trifluoromethylphenylsulfonyl chloride in place of sulfamoyl chloride, 1[[o-(trifluoromethyl)phenyl]-sulfonyl]-4-[[4-[[-7-(trifluoromethyl)-4-quinolinyl]-amino]-phenyl]sulfonyl]piperazine is obtained.

EXAMPLE 16

1-[(2-propyl-4-bromophenyl)sulfonyl]-4-[[4-[[7-chloro-4-quinolinyl]amino]phenyl]sulfonyl]-piperazine In the manner given in Example 13 but using 2-propyl-4-bromophenylsulfonyl chloride in place of sulfamoyl chloride and [[4-[(7-chloro-4-quinolinyl)amino]-phenyl]sulfonyl]piperazine in place of [[4-[(7-trifluoromethyl-4-quinolinyl]amino]sulfonyl]-piperazine, 1-[(2-propyl-4-bromophenyl)sulfonyl]-4-[[4-[[7-chloro-4-quinolinyl]amino]phenyl]sulfonyl]-piperazine is obtained.

EXAMPLE 17

1-[[(m-trifluoromethylphenyl)amino]carbonyl]-4[[4-[[7-(trifluoromethyl)-4-quinolinyl]amino]phenyl]-sulfonyl]-piperazine To [[4-[(7-trifluoromethyl-4-quinolinyl)amino]phenyl]sulfonyl]piperazine (prepared in Example 9, part D) in methylene chloride is added dropwise, at room temperature, m-trifluoromethylphenyl isocyanate in methylene chloride solution. The reaction is conducted in an atmosphere of nitrogen at room temperature for 1-5 hours. 1[[(m-Trifluoromethylphenyl)amino]carbonyl]-4-[[4-[[7-(trifluoromethyl)-4-quinolinyl]amino]phenyl]sulfonyl]piperazine is isolated by conventional methods, e.g., filtration, chromatography.

EXAMPLE 18

1-[[(2,4-diethylphenyl)amino]carbonyl]-4-[[7-chloro-4-quinolinyl]amino]phenyl]sulfonyl]-piperazine In the manner given in Example 17 but using 2,4-diethylphenylisocyanate in place of m-tri-fluoromethylphenylisocyanate and [[4-[(7-chloro-4-quinolinyl)amino]phenyl]sulfonyl]piperazine in place of [[4-[(7-trifluoromethyl-4-quinolinyl)amino]phenyl]sulfonyl]piperazine, 1-[[2,4-diethylphenyl)amino]carbonyl]-4-[[4-[[7-chloro-4-quinolinyl]amino]phenyl]sulfonyl]piperazine is obtained.

EXAMPLE 19

1-[[(4-chlorophenyl)amino]carbonyl]-4[[4-[[7-(trifluoromethyl)-4-quinolinyl]amino]phenyl]sulfonyl]piperazine In the manner given in Example 17 but using 4-chlorophenylisocyanate in place of m-trifluoromethylphenylisocyanate, 1-[[(4-chlorophenyl)amino]carbonyl]-4-[[4-[[7-(trifluoromethyl)-4-quinolinyl]-amino]phenyl]sulfonyl]piperazine is obtained.

EXAMPLE 20

1[[(3,4-dichlorophenyl)amino]carbonyl]-4-[[4-[[7-chloro-4-quinolinyl]amino]phenyl]sulfonyl]-piperazine In the manner of Example 18 but using 3,4-dichlorophenylisocyanate in place of 2,4-diethylphenylisocyanate, 1[[(3,4-dichlorophenyl)amino]carbonyl]-4-[[4-[[7-chloro-4-quinolinyl]amino]phenyl]sulfonyl]piperazine is obtained.

EXAMPLE 21

1-(p-propoxyphenyl)-4-[[4-[[7-chloro-4-quinolinyl]amino]phenyl]sulfonyl]piperazine

A.

1-[(p-nitrophenyl)sulfonyl]-4-(p-propoxyphenyl)piperazine

In the manner given in Example 1A, p-nitrobenzenesulfonyl chloride, 1-(p-propoxyphenyl)-piperazine and triethylamine are stirred at reflux to give 1-[(p-nitrophenyl)sulfonyl]-4-(p-propoxy-phenyl)piperazine.

B.

1-[(p-aminophenyl)sulfonyl]-4-(p-propoxyphenyl)piperazine

In the manner given in Example 1B, 1[(p-nitrophenyl)sulfonyl]-4-(p-propoxyphenyl)piperazine is reduced with hydrogen over platinum oxide catalyst (PtO2) to give 1-[(p-aminophenyl)sulfonyl]-4-(p-propoxyphenyl)piperazine.

C.

1-(p-propoxyphenyl)-4-[[4-[[7-chloro-4-quinolinyl]amino]phenyl]sulfonyl]piperazine In the manner given in Example 1C, 4,7-dichloroquinoline is heated with 1-[(p-aminophenyl)sulfonyl]-4-(p-propoxyphenyl)piperazine to give 1-(p-propoxyphenyl)-4-[[4-[[7-chloro-4-quinolinyl]amino]phenyl]-sulfonyl]piperazine.

EXAMPLE 22

1-(3,5-dipropylphenyl)-4-[[4-[[7-(trifluoromethyl)-4-quinolinyl]amino]phenyl]sulfonyl]piperazine

A.

1-[(p-nitrophenyl)sulfonyl]-4-(3,5-dipropylphenyl)piperazine

In the manner given in Example 1A, p-nitrobenzenesulfonyl chloride, 1-(3,5-dipropylphenyl)-piperazine and triethylamine are stirred at reflux to give 1-[(p-nitrophenyl)sulfonyl]-4-(3,5-dipropylphenyl)piperazine.

B.

1-[(p-aminophenyl)sulfonyl]-4-(3,5-dipropylphenyl)piperazine

In the manner given in Example 1B, 1-[(p-nitrophenyl)sulfonyl]-4-(3,5-dipropylphenyl)piperazine is reduced with hydrogen over PtO2 to give 1-[(p-aminophenyl)sulfonyl]-4-(3,5-dipropylphenyl)piperazine.

C.

1-(3,5-dipropylphenyl)-4-[[4-[[7-(trifluoromethyl)-4-quinolinyl]amino]phenyl]sulfonyl]-piperazine In the manner given in Example 1C, 4-chloro-7-trifluoromethylquinoline is heated with 1-[(p-aminophenyl)sulfonyl]-4-(3,5-dipropylphenyl)piperazine to give 1-(3,5-dipropylphenyl)-4-[[4-[[7-(trifluoromethyl)-4-quinolinyl]amino]phenyl]sulfonyl]piperazine.

EXAMPLE 23

1-[3,5-di(trifluoromethyl)phenyl]-4-[[4-[[7-chloro-4-quinolinyl]amino]phenyl]sulfonyl]piperazine

A.

1-[(p-nitrophenyl)sulfonyl]-4-[3,5-di(trifluoromethyl)phenyl]piperazine

In the manner given in Example 1A, p-nitrobenzenesulfonyl chloride, 1-[3,5-di(trifluoromethyl)phenyl]piperazine and triethylamine are stirred at reflux to give 1-[(p-nitrophenyl)sulfonyl]-4-[3,5-di(trifluoromethyl)phenyl]piperazine.

B.

1-[(p-aminophenyl)sulfonyl]-4-[3,5-di(trifluoromethyl)phenyl]piperazine

In the manner given in Example 5B, 1-[(p-nitrophenyl)sulfonyl]-4-[3,5-di(trifluoromethyl)-phenyl]piperazine is reduced with hydrogen over PtO2 to give 1-[(p-aminophenyl)sulfonyl]-4-[3,5-di(trifluoromethyl)-phenyl]piperazine.

C.

1-[3,5-di(trifluoromethyl)phenyl]-4-[[4-[[7-chloro-4-quinolinyl]amino]phenyl]sulfonyl]piperazine In the manner given in Example 1C, 4,7-dichloroquinoline is heated with 1-[(p-aminophenyl)sulfonyl]-4-[3,5-di(trifluoromethyl)phenyl]piperazine, to give 1-[3,5-di(trifluoromethyl)phenyl]-4-[[4-[[7-chloro-4-quinolinyl]amino]phenyl]sulfonyl]piperazine.

EXAMPLE 24

1-[(2-ethylthio-4-bromo)phenyl]-4-[[4-[[7-(trifluoromethyl)-4-quinolinyl]amino]phenyl-sulfonyl]piperazine

A.

1-[(p-nitrophenyl)sulfonyl]-4-[(2-ethylthio-4-bromo)phenyl]piperazine

In the manner given in Example 1A, p-nitrobenzenesulfonyl chloride, 1-[(2-ethyl-4-bromo)-phenyl]piperazine and triethylamine are stirred at reflux to give 1-[(p-nitrophenyl)sulfonyl]-4-[(2-ethyl-4-bromo)-phenyl]piperazine.

B.

1-[(p-aminophenyl)sulfonyl]-4-[(2-ethyl-4-bromo)-phenyl]piperazine

In the manner given in Example 5B, 1-[(p-nitrophenyl)sulfonyl]-4-[(2-ethylthio-4-bromo)phenyl]-piperazine is reduced with $TiCl_3$ to give 1-[(p-aminophenyl)sulfonyl]-4-[(2-ethyl-4-bromo)phenyl]piperazine.

C.

1-[(2-ethylthio-4-bromo)phenyl]-4-[[4-[[7-(trifluoromethyl)-4-quinolinyl]amino]phenyl]sulfonyl]piperazine In the manner given in Example 1C, 4-chloro-7-(trifluoromethyl)quinoline is heated with 1-[(p-aminophenyl)sulfonyl]-4-[(2-ethylthio-4-bromo)phenyl]piperazine, previously reacted with acetyl chloride, to give 1-[(2-ethylthio-4-bromo)phenyl]-4-[[4-[[7-(trifluoromethyl)-4-quinolinyl]amino]phenyl]sulfonyl]piperazine.

EXAMPLE 25

1-[(4,6-dimethyl-2-pyrimidinyl)]-4-[[4-[[7-chloro-4-quinolinyl]amino]phenyl]sulfonyl]piperazine In the manner given in Example 9, part E, 2-chloro-4,6-dimethylpyrimidine is heated with [[4-[(7-chloro-4-quinolinyl)amino]phenyl]sulfonyl]piperazine to give 1-[(4,6-dimethyl-2-pyrimidinyl)]-4-[[4-[[7-chloro-4-quinolinyl]amino]phenyl]sulfonyl]piperazine.

EXAMPLE 26

1-[(3-ethyl-4-propoxy-2-pyridinyl)]-4-[[4-[[7-(trifluoromethyl)-4-quinolinyl]amino]phenyl]sulfonyl]piperazine In the manner given in Example 9E, but using 2-chloro-3-ethyl-4-propoxypyridine in place of 2-chloropyrimidine, 1-[(3-ethyl-4-propoxy-2-pyridinyl)]-4-[[4-[[7-(trifluoromethyl)-4-quinolinyl]amino]phenyl]-sulfonyl]piperazine is obtained.

EXAMPLE 27

1-[(2,4-dimethoxyphenyl)sulfonyl]-4-[[4-[[7-chloro-4-quinolinyl]amino]phenyl]sulfonyl]piperazine

A.

1-[(p-nitrophenyl)sulfonyl]-4-[(2,4-dimethoxyphenyl)-sulfonyl]piperazine

In the manner given in Example 1A, p-nitrobenzenesulfonyl chloride, 1-[(2,4-dimethoxyphenyl)-sulfonyl]piperazine and triethylamine are stirred at reflux to give 1-[(p-nitrophenyl)sulfonyl]-4-[(2,4-dimethoxyphenyl)sulfonyl]piperazine.

B.

1-[(p-aminophenyl)sulfonyl]-4-[(2,4-dimethoxyphenyl)-sulfonyl]piperazine

In the manner given in Example 5B, 1-[(p-nitrophenyl)sulfonyl]-4-[(2,4-dimethoxyphenyl)sulfonyl]piperazine is reduced with $TiCl_3$ to give 1-[(p-aminophenyl)sulfonyl]-4-[(2,4-dimethoxy-phenyl)sulfonyl]piperazine.

C.

1-[(2,4-dimethoxyphenyl)sulfonyl]-4-[[4-[[7-chloro-4-quinolinyl]amino]phenyl]sulfonyl]-piperazine In the manner given in Example 1C, 4,7-dichloroquinoline is heated with 1-[(p-aminophenyl)sulfonyl]-4-[(2,4-dimethoxyphenyl)sulfonyl]piperazine to give 1-[(2,4-dimethoxyphenyl)sulfonyl]-4-[[4-[[7-chloro-4-quinolinyl]amino]phenyl]sulfonyl]piperazine.

EXAMPLE 28

1-[(3-fluoro-4-propylphenyl)sulfonyl]-4-[[4-[[7-(trifluoromethyl)-4-quinolinyl]amino]phenyl]sulfonyl]piperazine

A.

1-[(p-nitrophenyl)sulfonyl]-4-[(3-fluoro-4-propyl-phenyl)sulfonyl]piperazine

In the manner given in Example 1A, p-nitrobenzenesulfonyl chloride, 1-[(3-fluoro-4-propylphenyl)sulfonyl]piperazine and triethylamine are stirred at reflux to give 1-[(p-nitrophenyl)sulfonyl]-4-[(3-fluoro-4-propylphenyl)sulfonyl]piperazine.

B.

1-[(p-aminophenyl)sulfonyl]-4-[(3-fluoro-4-propyl-phenyl)sulfonyl]piperazine

In the manner given in Example 5B, 1-[(p-nitrophenyl)sulfonyl]-4-[(3-fluoro-4-propylphenyl)-sulfonyl]piperazine is reduced with $TiCl_3$ to give 1-[(p-aminophenyl)sulfonyl]-4-[(3-fluoro-4-propylphenyl)sulfonyl]piperazine.

C.

1-[(3-fluoro-4-propylphenyl)sulfonyl]-4-[[4-[[7-(trifluoromethyl)-4-quinolinyl]amino]phenyl]-sulfonyl]piperazine In the manner given in Example 1C, 4-chloro-7-(trifluoromethyl)quinoline is heated with 1-[(p-aminophenyl)sulfonyl]-4-[(3-fluoro-4-propylphenyl)-sulfonyl]piperazine to give 1-[(3-fluoro-4-propylphenyl)-sulfonyl]-4-[[4-[[7-(trifluoromethyl)-4-quinolinyl]amino]phenyl]sulfonyl]piperazine.

EXAMPLE 29

1-[(dipropylamino)sulfonyl]-4-[[4-[[7-chloro-4-quinolinyl]amino]phenyl]sulfonyl]piperazine In the manner given in Example 13 but using dipropylsulfamoyl chloride in place of dimethylsulfamoyl chloride and [[4-[[7-chloro-4-quinolinyl]-amino]phenyl]sulfonyl]piperazine in place of [[4-[(7-trifluoromethyl-4-quinolinyl)amino]phenyl]-sulfonyl]piperazine, 1-[(dipropylamino)sulfonyl]-4-[[4-[[7-chloro-4-quinolinyl]amino]phenyl]sulfonyl]-piperazine is obtained.

EXAMPLE 30

1-[[(3propoxy-5-fluorophenyl)amino]carbonyl]-4-[[4-[[7-chloro-4-quinolinyl]amino]phenyl]-sulfonyl]piperazine

A.

1-[(p-nitrophenyl)sulfonyl]-4-[[(3-propoxy-5-fluorophenyl)amino]carbonyl]piperazine In the manner given in Example 1A, p-nitrobenzenesulfonyl chloride, 1-[[(3-propoxy-5-fluorophenyl)amino]carbonyl]piperazine and triethylamine are stirred at reflux to give 1-[(p-nitrophenyl)-sulfonyl]-4-[[(3-propoxy-5-fluorophenyl)amino]-carbonyl]piperazine.

B.

1-[(p-aminophenyl)sulfonyl]-4-[[(3-propoxy-5-fluorophenyl)amino]carbonyl]piperazine In the manner given in Example 5B, 1-[(p-nitrophenyl)sulfonyl]-4-[[(3-propoxy-5-fluorophenyl)amino]carbonyl]piperazine is reduced with $TiCl_3$ to give 1-[(p-aminophenyl)sulfonyl]-4-[[(3-propoxy-5-fluorophenyl)amino]carbonyl]piperazine.

C.

1-[[(3-propoxy-5-fluorophenyl)amino]carbonyl]-4-[[4-[[7-chloro-4-quinolinyl]amino]phenyl]-sulfonyl]piperazine In the manner given in Example 1C, 4,7-dichloroquinoline is heated with 1-[(p-aminophenyl)-sulfonyl]-4-[[(3-propoxy-5-fluorophenyl)amino]-carbonyl]piperazine to give 1-[[(3-propoxy-5-fluorophenyl)amino]carbonyl]-4-[[4-[[7-chloro-4-quinolinyl]amino]phenyl]sulfonyl]piperazine.

EXAMPLE 31

1-[(4-ethylphenylsulfonamido)carbonyl]-4-[[4-[[7-trifluoromethyl-4-quinolinyl]amino]phenyl]-sulfonyl]piperazine In the manner given in Example 17 but using 4-ethylphenylsulfonylisocyanate in place of m-trifluoromethylphenylisocyanate, 1-[(4-ethylphenyl-sulfonamido)carbonyl]-4-[[4-[[7-trifluoromethyl-4-quinolinyl]amino]phenyl]sulfonyl]piperazine is obtained.

In the manner given in Examples 1 through 5, 9, 13, and 17, other compounds of formula III can be prepared. Representative compounds thus obtained include:

1-(3-methoxyphenyl)-4-[[4-[[7-(trifluoromethyl)-4-quinolinyl]amino]phenyl]sulfonyl]piperazine
1-(4-ethoxyphenyl)-4-[[4-[[7-(trifluoromethyl)-4-quinolinyl]amino]phenyl]sulfonyl]piperazine
1-(3,5-dipropoxyphenyl)-4-[[4-[[7-(trifluoromethyl)-4-quinolinyl]amino]phenyl]sulfonyl]piperazine
1-(2-bromo-4-fluorophenyl)-4-[[4-[[7-(trifluoromethyl)-4-quinolinyl]amino]phenyl]sulfonyl]piperazine
1-(2-fluoro-4-chlorophenyl)-4-[[4-[[7-(trifluoromethyl)-4-quinolinyl]amino]phenyl]sulfonyl]-piperazine
1-[4-ethyl-1,3,5-triazin-2-yl]-4-[[4-[[7-(trifluoromethyl)-4-quinolinyl]amino]phenyl]sulfonyl]piperazine
1-[4,6-dibromo-1,3,5-triazin-2-yl]-4-[[4-[[7-(trifluoromethyl)-4-quinolinyl]amino]phenyl]sulfonyl]-piperazine
1-[4-methyl-6-chloro-1,3,5-triazin-2-yl]-4-[[4-[[7-(trifluoromethyl)-4-quinolinyl]amino]phenyl]sulfonyl]-piperazine
1-[3-ethylpyrazinyl]-4-[[4-[[7-(trifluoromethyl)-4-quinolinyl]amino]phenyl]sulfonyl]piperazine
1-[3,6-dichloropyrazin-2-yl]-4-[[4-[[7-(trifluoromethyl)-4-quinolinyl]amino]phenyl]sulfonyl]-piperazine
1-[3-ethoxy-5-chloropyrazin-2-yl]-4-[[4-[[7-(trifluoromethyl)-4-quinolinyl]amino]phenyl]-sulfonyl]-piperazine
1-[3,4,5-trichloropyridin-2-yl]-4-[[4-[[7-(trifluoromethyl)-4-quinolinyl]amino]phenyl]sulfonyl]piperazine
1-[3,5-dibromopyridin-2-yl]-4-[[4-[[7-(trifluoromethyl)-4-quinolinyl]amino]phenyl]sulfonyl]piperazine
1-[3,5-difluoropyridin-2-yl]-4-[[4-[[7-(trifluoromethyl)-4-quinolinyl]amino]phenyl]sulfonyl]piperazine
1-[3-fluoro-1,2,4-as-triazin-5-yl]-4-[[4-[[7-(trifluoromethyl)-4-quinolinyl]amino]phenyl]sulfonyl]piperazine
1-[5-trifluoromethyl-as-triazin-3-yl]-4-[[4-[[7-(trifluoromethyl)-4-quinolinyl]amino]phenyl]sulfonyl]-piperazine
1-[6-methoxypyrimidin-2-yl]-4-[[4-[[7-(trifluoromethyl)-4-quinolinyl]amino]phenyl]sulfonyl]-piperazine
1[4,6-dipropylpyrimidin-2-yl]-4-[[4-[[7-(trifluoromethyl)-4-quinolinyl]amino]phenyl]sulfonyl]piperazine
1-[5-ethoxypyrimidin-2-yl]-4-[[4-[[7-(trifluoromethyl)-4-quinolinyl]amino]phenyl]sulfonyl]piperazine
1-[4-methyl-5-fluoropyrimidin-2-yl]-4-[[4-[[7-(trifluoromethyl)-4-quinolinyl]amino]phenyl]sulfonyl]-piperazine
1-[(2,4-dichlorophenyl)sulfonyl]-4-[[4-[[7-(trifluoromethyl)-4-quinolinyl]amino]phenyl]sulfonyl]-piperazine
1-[(3-bromo-4-fluorophenyl)sulfonyl]-4-[[4-[[7-(trifluoromethyl)-4-quinolinyl]amino]phenyl]-sulfonyl]-piperazine
1-[(2-methyl-3-fluorophenyl)sulfonyl]-4-[[4-[[7-(trifluoromethyl)-4-quinolinyl]amino]phenyl]sulfonyl]-piperazine
1-[(3-propoxy-4-methylphenyl)sulfonyl]-4-[[4-[[7-(trifluoromethyl)-4-quinolinyl]amino]phenyl]sulfonyl]-piperazine
1-[(3,4-dibromophenyl)sulfonyl]-4-[[4-[[7-(trifluoromethyl)-4-quinolinyl]amino]phenyl[sulfonyl]piperazine
1-[(dipropylamino)sulfonyl]-4-[[4-[[7-(trifluoromethyl)-4-quinolinyl]amino]phenyl]sulfonyl]piperazine
1-[[(m-ethoxyphenyl)amino]carbonyl]-4-[[4-[[7-(trifluoromethyl)-4-quinolinyl]amino]phenyl]sulfonyl]-piperazine
1-[[(3-bromo-4-methoxyphenyl)amino]carbonyl]-4-[[4-[[7-(trifluoromethyl)-4-quinolinyl]amino]phenyl]-sulfonyl]piperazine
1-[[(3,4-dichlorophenyl)amino]carbonyl]-4-[[4-[[7-(trifluoromethyl)-4-quinolinyl]amino]phenyl]-sulfonyl]-piperazine
1-[[(2,4-difluorophenyl)amino]carbonyl]-4-[[4-[[7-(trifluoromethyl)-4-quinolinyl]amino]phenyl]-sulfonyl]-piperazine
1-[[(2,3-dimethoxyphenyl)amino]carbonyl]-4-[[4-[[7-(trifluoromethyl)-4-quinolinyl]amino]phenyl]-sulfonyl]piperzine
1-[(p-methylphenyl)sulfonyl]-4-[[4-[[7-(trifluoromethyl)-4-quinolinyl]amino]phenyl]sulfonyl[piperazine
1-[[(m-fluorophenyl)amino]carbonyl]-4-[[4-[[7-(trifluoromethyl)-4-quinolinyl]amino]phenyl]sulfonyl]-piperazine
1-(3-methoxyphenyl)-4-[[4-[[7-chloro-4-quinolinyl]amino]phenyl]sulfonyl]piperazine 1-(4-propoxyphenyl)-4-[[4-[[7-chloro-4-quinolinyl]-amino]phenyl]sulfonyl]piperazine
1-(3,5-diethoxyphenyl)-4-[[4-[[7-chloro-4-quinolinyl]amino]phenyl]sulfonyl]piperazine
1-(2-bromo-4-fluorophenyl)-4-[[4-[[7-chloro-4-quinolinyl]amino]phenyl]sulfonyl]piperazine
1-[(2-fluoro-4-chlorophenyl)]-4-[[4-[[7-chloro-4-quinolinyl]amino]phenyl]sulfonyl]piperazine
1-(4-ethyl-1,3,5-triazin-2-yl)-4-[[4-[[7-chloro-4-quinolinyl]amino]phenyl]sulfonyl]piperazine
1-[4,6-dibromo-1,3,5-triazin-2-yl]-4-[[4-[[7-chloro-4-quinolinyl]amino]phenyl]sulfonyl]piperazine
1-[4-methyl-6-chloro-1,3,5-triazin-2-yl]-4-[[4-[[7-chloro-4-quinolinyl]amino]phenyl]sulfonyl]piperazine
1-[3-ethylpyrazin-2-yl]-4-[[4-[[7-chloro-4-quinolinyl]-amino]phenyl]sulfonyl]piperazine
1-[3,6-dichloropyrazin-2-yl]-4-[[4-[[7-chloro-4-quinolinyl]amino]phenyl]sulfonyl]piperazine
1-[3-ethoxy-5-chloropyrazin-2-yl]-4-[[4-[[7-chloro-4-quinolinyl]amino]phenyl]sulfonyl]piperazine
1-[3,4,5-trichloropyridin-2-yl]-4-[[4-[[7-chloro-4-quinolinyl]amino]phenyl]sulfonyl]piperazine  1-[3,5-dibromopyridin-2-yl]-4-[[4-[[7-chloro-4-quinolinyl]amino]phenyl]sulfonyl]piperazine
1-[3,5-dimethylpyridin-2-yl]-4-[[4-[[7-chloro-4-quinolinyl]amino]phenyl]sulfonyl]piperazine
1-[3-fluoro-as-triazin-5-yl]-4-[[4-[[7-chloro-4-quinolinyl]amino]phenyl]sulfonyl]piperazine
1-[5-trifluoromethyl-as-triazin-3-yl]-4-[[4-[[7-chloro-4-quinolinyl]amino]phenyl]sulfonyl]piperazine
1-[6-methoxypyrimidin-2-yl]-4-[[4-[[7-chloro-4-quinolinyl]amino]phenyl]sulfonyl]piperazine
1-[4,6-dipropylpyrimidin-2-yl]-4-[[4-[[7-chloro-4-quinolinyl]amino]phenyl]sulfonyl]piperazine
1-[5-ethoxypyrimidin-2-yl]-4-[[4-[[7-chloro-4-quinolinyl]amino]phenyl]sulfonyl]piperazine
1-[4-methyl-5-fluoropyrimidin-2-yl]-4-[[4-[[7-chloro-4-quinolinyl]amino]phenyl]sulfonyl]-piperazine
1-[(2,4-dichlorophenyl)sulfonyl]-4-[[4-[[7-chloro-4-quinolinyl]amino]phenyl]sulfonyl]piperazine
1-[(3-bromo-4-fluorophenyl)sulfonyl]-4-[[4-[[7-chloro-4-quinolinyl]amino]phenyl]sulfonyl]-piperazine
1-[(2-methyl-3-fluorophenyl)sulfonyl]-4-[[4-[[7-chloro-4-quinolinyl]amino]phenyl]sulfonyl]-piperazine
1-[(3-propoxy-4-methyl)sulfonyl]-4-[[4-[[7-chloro-4-quinolinyl]amino]phenyl]sulfonyl]piperazine
1-[3,5-dibromophenyl]-4-[[4-[[7-chloro-4-quinolinyl]-amino]phenyl]sulfonyl]piperazine
1-[(dipropylamino)sulfonyl]-4-[[4-[[7-chloro-4-quinolinyl]amino]phenyl]sulfonyl]piperazine
1-[[(m-ethoxyphenyl)amino]carbonyl]-4-[[4-[[7-chloro-4-quinolinyl]amino]phenyl]sulfonyl]piperazine
[[(3-bromo-4-methoxyphenyl)amino]carbonyl]-4-[[4-[[7-chloro-4-quinolinyl]amino]phenyl]sulfonyl]-piperazine
1-[[(3,4-dichlorophenyl)amino]carbonyl]-4-[[4-[[7-chloro-4-quinolinyl]amino]phenyl]sulfonyl]piperazine
1-[[(2,4-difluorophenyl)amino]carbonyl]-4-[[4-[[7-chloro-4-quinolinyl]amino]phenyl]sulfonyl]-piperazine
1-[[(2,3-dimethoxyphenyl)amino]carbonyl]-4-[[4-[[7-chloro-4-quinolinyl]amino]phenyl]sulfonyl]-piperazine and the like.

Isolation and purification of the compounds of this invention are carried out by conventional means using chromatography, recrystallization, and the like.

On occasion, the compounds or their acid addition salts in their crystalline state are isolated as solvates, i.e., they have discrete quantity of solvent, e.g., water, ethanol, and the like, associated physically, and thus removable without effective alteration of the chemical entity per se. The invention is meant to encompass all such forms of the compounds.

The pharmacologically acceptable acid addition salts of compounds of formula III (including the preferred compounds of formulae IIIA, IIIB and IIIC) can be prepared and isolated by conventional processes, such as reacting a compound of formula III with a selected pharmacologically acceptable acid. Such acids include hydrochloric, hybrobromic, phosphoric, sulfuric, acetic, tartaric, lactic, citric, malic, maleic, methanesulfonic, benzenesulfonic, pamoic cyclohexanesulfamic acids, toluenesulfonic, and the like. The reaction is conveniently performed in an organic solvent, e.g., ether, dioxane or tetrahydrofuran, ethanol, methanol, ethyl acetate; the salts can be recovered by crystallization, precipitation or evaporation of the solvent. These salts are useful in the same manner as the free base.

The following examples illustrate formulations which are useful for the practice of this invention:

EXAMPLE 32

One thousand tablets for oral use, each containing 50 mg of 1-[2-methylphenyl]-4-[[4-[[7-(trifluoromethyl)-4-quinolinyl]amino]phenyl]-sulfonyl]piperazine as essential active ingredient are prepared from the following ingredients:

| Essential active ingredient | 50 g |
|---|---|
| Dicalcium phosphate | 150 g |
| Methylcellulose, U.S.P. (15 cps) | 6.5 g |
| Talc | 20 g |
| Calcium stearate | 2.5 g |

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of severe hypertension and adult humans at a dose of 1 tablet 2 or 3 times a day.

EXAMPLE 33

One thousand two-piece hard gelatin capsules for oral use, each capsule containing 75 mg of 1-[2-methoxyphenyl]-4-[[4-[[7-(trifluoromethyl)-4-quinolinyl]amino]phenyl]sulfonyl]piperazine as essential active ingredient are prepared from the following ingredients:

| Essential active ingredient | 75 g |
|---|---|
| Lactose, U.S.P. | 100 g |
| Starch, U.S.P. | 10 g |
| Talc, U.S.P. | 50 g |
| Calcium stearate | 1 g |

The finely powdered materials are mixed thoroughly, then filled into hard gelatin capsules of appropriate size.

A satisfactory clinical response is obtained in adults showing hypertension with 1 capsule 4 times a day.

EXAMPLE 34

One-piece soft elastic capsules for oral use, each containing 10 mg of 1-(4-fluorophenyl)-4-[[4-[[7-(trifluoromethyl)-4-quinolinyl]amino]phenyl]sulfonyl]piperazine as essential active ingredient are prepared in the usual manner by first dispersing the powdered active material in sufficient corn oil to render the material capsulatable.

One capsule 4 times a day is useful in the treatment of moderate hypertension in adult humans.

EXAMPLE 35

An aqueous oral preparation containing in each teaspoonful (5 ml) 15 mg of 1-(2-pyridinyl)-4-[[4-[[7-(trifluoromethyl)-4-quinolinyl]amino]phenyl]sulfonyl]piperazine as essential active ingredient is prepared from the following ingredients:

| Essential active ingredient | | |
|---|---|---|
| hydrochloride | 30 | g |
| Methylparaben, U.S.P. | 7.5 | g |
| Propylparaben, U.S.P. | 2.5 | g |
| Saccharin sodium | 12.5 | g |
| Cyclamate sodium | 2.5 | g |
| Glycerin | 3000 | ml |
| Tragacanth powder | 10 | g |
| Orange oil flavor | 10 | g |
| F.D. and C. Orange dye | 7.5 | g |
| Deionized water, q.s. to | 10,000 | ml |

The foregoing aqueous preparation is useful in the treatment of adult hypertension at a dose of 1 teaspoonful 4 times a day.

EXAMPLE 36

One thousand tablets for oral administration, each containing 5 mg of 1-(4-fluorophenyl)-4-[[4-[[7-(trifluoromethyl)-4-quinolinyl]amino]phenyl]sulfonyl]piperazine as active ingredient and 16.2 mg of phenobarbital are prepared from the following ingredients:

| Essential active ingredient, | | |
|---|---|---|
| micronized | 5 | g |
| Phenobarbital | 16.2 | g |
| Lactose | 150 | g |
| Starch | 15 | g |
| Magnesium stearate | 1.5 | g |

The ingredients are thoroughly mixed and slugged. The slugs are broken down by forcing through a screen and the resulting granules are then compressed into tablets.

These tablets are useful in treating hypertensive dogs at a dose of 1 to 3 tablets depending on the weight of the animal and its condition.

EXAMPLE 37

A sterile aqueous suspension suitable for intramuscular muscular injection and containing in each milliliter, 2 mg of 1-(4-fluorophenyl)-4-[[4-[[7-(trifluoromethyl)-4-quinolinyl]amino]phenyl]sulfonyl]piperazine as essential active ingredient is prepared from the following ingredients:

| Essential active ingredient | 2 | g |
|---|---|---|
| Polyethylene glycol 4000, U.S.P. | 3 | g |
| Sodium chloride | 0.9 | g |

-continued

| Polysorbate 80, U.S.P. | 0.4 g |
|---|---|
| Sodium metabisulfite | 0.1 g |
| Methylparaben, U.S.P. | 0.18g |
| Propylparaben, U.S.P. | 0.02g |
| Water for injection, q.s. to | 1000 ml |

The preceding sterile injectable is useful in the treatment of severe hypertension in humans at a dose of 1 or 2 ml.

EXAMPLE 38

One thousand suppositories, each weighing 2.5 g and containing 100 mg of 1-(3-chlorophenyl)-4-[[4-[[7-(trifluoromethyl)-4-quinolinyl]amino]phenyl]sulfonyl]piperazine as essential active ingredient are prepared from the following ingredients:

| Essential active ingredient | 100 g |
|---|---|
| Propylene glycol | 165 g |
| Polyethylene glycol 4000, q.s. | 2500 g |

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of hypertension at a dose of 1 suppository rectally three times a day.

EXAMPLE 39

One thousand hard gelatin capsules for oral use, each containing 10 mg of 1-(4-fluorophenyl)-4-[[4-[[7-(trifluoromethyl)-4-quinolinyl]amino]phenyl]sulfonyl]piperazine as essential active ingredient and 25 mg of hydrochlorothiazide are prepared from the following ingredients:

| Essential active ingredient, | |
|---|---|
| micronized | 10 g |
| Hydrochlorothiazide | 25 g |
| Starch | 125 g |
| Talc | 25 g |

One capsule 4 times a day is useful in the relief of moderate hypertension in adult humans.

EXAMPLE 40

Ten thousand scored tablets for oral use, each containing 25 mg of 1-(4-fluorophenyl)-4-[[4-[[7-(trifluoromethyl)-4-quinolinyl]amino]phenyl]sulfonyl]piperazine as essential active ingredient and 0.08 mg of reserpine, are prepared from the following ingredients and using the procedure of Example 32:

| Essential active ingredient, | | |
|---|---|---|
| micronized | 250 | g |
| Reserpine | 0.8 | g |
| Lactose | 1500 | g |
| Corn Starch | 500 | g |
| Talc | 500 | g |
| Calcium stearate | 25 | g |

This combination of active materials is effective in reducing hypertension in adult humans. The dose is one-half to two tablets 3 times a day depending on the severity of the condition.

EXAMPLE 41

Ten thousand tablets for oral use, each containing 60 mg of 1-(2-methylphenyl)-4-[[4-[[7-(trifluoromethyl)-4-quinolinyl]amino]phenyl]sulfonyl]piperazine as the essential active ingredient and 25 mg melitracen, are prepared from the following ingredients and using the procedure of Example 32:

| Essential active ingredient, | |
|---|---|
| micronized | 6000 g |
| Melitracen, powdered | 250 g |
| Lactose | 1000 g |
| Cornstarch | 500 g |
| Talc | 500 g |
| Calcium stearate | 25 g |

This tablet is useful in treating hypertensive adult humans suffering from depression by administering one tablet 3 times a day.

EXAMPLE 42

Ten thousand tablets for oral use, each containing 20 mg of 1-(dimethylaminosulfonyl)-4-[[4-[[7-(trifluoromethyl)-4-quinolinyl]amino]phenyl]sulfonyl]piperazine as essential active ingredient and 320 mg acetominophen, are prepared from the following ingredients and using the procedure of Example 32:

| Essential active ingredient, | |
|---|---|
| finely powdered | 200 g |
| Acetaminophen, | |
| finely powdered | 3200 g |
| Corn starch | 500 g |
| Talc | 500 g |
| Calcium stearate | 50 g |

This tablet is useful in treating hypertension in an adult patient by administering one or two tablets 3 times a day depending on the severity of the condition.

EXAMPLE 43

Following the procedure of the preceding Examples 32 to 42 but substituting other compounds of formula III, or their pharmacologically acceptable acid addition salts, useful formulations can be prepared. The following list of compounds is representative:

1-[(4-methylphenyl)sulfonyl]-4-[[4-[[7-(trifluoromethyl)-4-quinolinyl]amino]phenyl]sulfonyl]piperazine
1-[[(3-trifluoromethylphenyl)amino]carbonyl]-4-[[4-[[7-(trifluoromethyl)-4-quinolinyl]amino]phenyl]sulfonyl]piperazine
1-[(4-chlorophenyl)sulfonyl]-4-[[4-[[7-chloro-4-quinolinyl]amino]phenyl]sulfonyl]piperazine
1-(3-chlorophenyl)-4-[[4-[[7-(trifluoromethyl)-4-quinolinyl]amino]phenyl]sulfonyl]piperazine
1-(2-pyrimidinyl)-4-[[4-[[7-(trifluoromethyl)-4-quinolinyl]amino]phenyl]sulfonyl]piperazine, and the like.

Although not necessary in the embodiments of the inventive concept, additional active ingredients are incorporated in the present pharmaceutical dosage unit forms as desired. Each pharmaceutical dosage unit form contains therein an amount within the following nontoxic effective ranges: antihypertensive and diuretic agents such as reserpine (0.05 to 1 mg), hydralazine (10 to 100 mg), methyldopa (100 to 250 mg), guanethidine (10 to 50 mg), hydrochlorothiazide (15 to 50 mg), and ethoxzolamide (50 to 150 mg); tranquilizers, antipsychotic and anti-anxiety agents such as chloropromazine (5 to 50 mg), thioridazine (5 to 100 mg), haloperidol (0.5 to 5 mg), meprobamate (100 to 400 mg), chlorodiazepoxide (5 to 50 mg), diazepam (2 to 15 mg), and ectylurea (100 to 300 mg); barbiturates such as phenobarbital (8 to 60 mg), butabarbital (8 to 60 mg) and amobarbital (16 to 120 mg); analgesics such as aspirin (150 to 600 mg) and acetaminophen (150 to 600 mg); or antidepressants such as amitriptyline hydrochloride (10 to 50 mg), methylphenidate hydrochloride (5 to 20 mg), d-amphetamine sulfate (2 to 15 mg), methamphetamine hydrochloride (2 to 15 mg) and melitracen (15 to 50 mg).

I claim:

1. A compound of the formula III

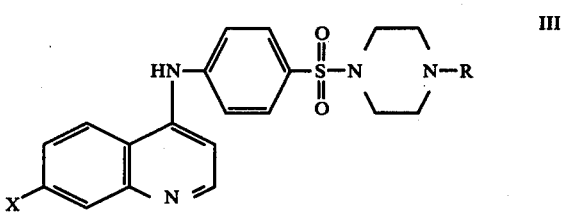

wherein X is chloro or trifluoromethyl; wherein R is
 (a) triazinyl;
 (b) pyrazinyl;
 (c) pyrimidinyl;
 (d) triazinyl, pyrazinyl, or pyrimidinyl substituted by one or two trifluoromethyl, alkyl, alkoxy, dialkylamino, alkylthio, or halo, wherein halo is fluoro, bromo, or iodo, wherein alkyl is of one to 3 carbon atoms, and wherein alkoxy is of one to 3 carbon atoms;
 (e) halopyridinyl of 1 to 4 halo atoms;
 (f) halopyridinyl of less than 4 halo atoms substituted by one or two trifluoromethyl, alkyl, alkoxy, dialkylamino, or alkylthio;
 (g)

wherein $R_1$ is phenyl, phenyl substituted with one or two halo, alkoxy, alkyl, trifluoromethylphenyl, or alkylphenyl, wherein alkyl, alkoxy and halo are as defined above; or
 (h) —$SO_2R_2$, wherein $R_2$ is dialkylamino, phenyl, substituted with one or two halo, alkyl, alkoxy, or trifluoromethylphenyl, wherein alkyl, alkoxy, and halo are as defined above; or the pharmacologically acceptable acid addition salts thereof.

2. A compound according to claim 1 of the formula IIIA

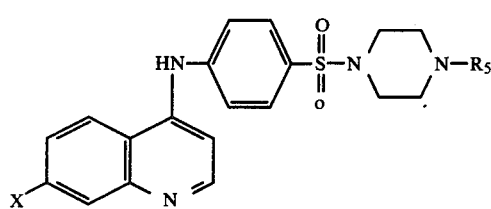

IIIA

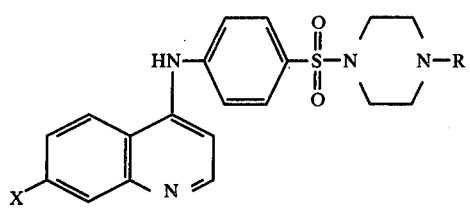

III wherein X is chloro or trifluoromethyl; wherein $R_5$ is
  (a) pyrimidinyl or the trifluoromethyl-, alkyl-, halo- or alkoxy-substituted derivatives thereof, wherein halo is chloro or fluoro and alkyl and alkoxy are of 1 to 3 carbon atoms;
  (b) halopyridinyl;
  (c) —$SO_2R_6$, wherein $R_6$ is dialkylamino, alkyl, alkoxy, phenyl, alkylphenyl, halophenyl, alkoxyphenyl, or trifluoromethylphenyl, in which alkoxy, alkyl and halo are defined as above; or the pharmacologically acceptable acid addition salts thereof.

3. A compound of claim 1 of the formula IIIC

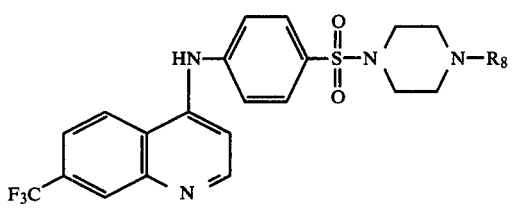

IIIC wherein $R_8$ is pyrimidinyl or pyrimidyl substituted with one or two trifluoromethyl, alkyl, alkoxy, or halo groups, in which alkyl and alkoxy are each of one to three carbon atoms, inclusive, and halo is fluoro or chloro; or the pharmacologically acceptable acid addition salts thereof.

4. The compound according to claim 3 wherein $R_8$ is 2-pyrimidinyl and the compound is therefore 1-(2-pyrimidinyl)-4-[[4-[[7-(trifluoromethyl)4-quinolinyl]amino]phenyl]sulfonyl]piperazine.

5. The compound according to claim 2 wherein $R_5$ is dimethylaminosulfonyl and X is trifluoromethyl, and the compound is therefore 1-(dimethylaminosulfonyl)-4-[[4-[[7-(trifluoromethyl)-4-quinolinyl]amino]phenyl]sulfonyl]piperazine.

6. The compound according to claim 2 wherein $R_5$ is [o-(trifluoromethyl)phenyl]sulfonyl and X is trifluoromethyl, and the compound is therefore 1-[[o-(trifluoromethyl)phenyl]sulfonyl]-4-[[4-[[7-(trifluoromethyl)-4-quinolinyl]amino]phenyl]sulfonyl]piperazine.

7. The compound according to claim 3 wherein $R_8$ is [(m-trifluoromethylphenyl)amino]carbonyl and the compound is therefore 1-[[(m-trifluoromethylphenyl)amino]carbonyl and the compound is therefore 1-[[(m-fluorophenyl)amino]carbonyl]-4-[[4-[[7-(trifluoromethyl)-4-quinolinyl]amino]phenyl]sulfonyl]piperazine.

8. A pharmaceutical dosage unit form for systemic administration to alleviate hypertension consisting essentially of an effective nontoxic amount of a compound of the formula III wherein X is chloro or trifluoromethyl; wherein R is
  (a) triazinyl;
  (b) pyrazinyl;
  (c) pyrimidinyl;
  (d) triazinyl, pyrazinyl, or pyrimidinyl substituted by one or two trifluoromethyl, alkyl, alkoxy, dialkylamino, alkylthio, or halo, wherein halo is fluoro, bromo, or iodo, wherein alkyl is of one to 3 carbon atoms, and wherein alkoxy is of one to 3 carbon atoms;
  (e) halopyridinyl of 1 to 4 halo atoms;
  (f) halopyridinyl of less than 4 atoms substituted by one or two trifluoromethyl, alkyl, alkoxy, dialkylamino, or alkylthio;
  (g)

—$CNHR_1$, wherein $R_1$ is phenyl, phenyl substituted with one or two halo, alkoxy, alkyl, trifluoromethylphenyl, or alkylphenyl, wherein alkyl, alkoxy and halo are as defined above; or
  (h) —$SO_2R_2$, wherein $R_2$ is dialkylamino, phenyl substituted with one or two halo, alkyl, alkoxy, or trifluoromethylphenyl, wherein alkyl, alkoxy, and halo are as defined above; or the pharmacologically acceptable acid addition salts thereof.

9. The composition according to claim 8 wherein the compound used in an effective non-toxic amount is that of the formula IIIA

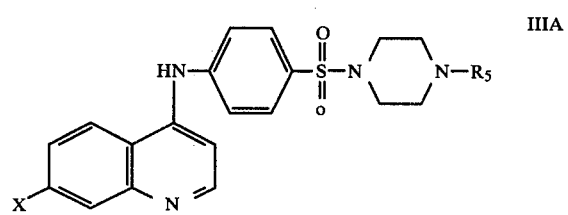

IIIA wherein X is chloro or trifluoromethyl; wherein $R_5$ is
  (a) pyrimidinyl or the trifluoromethyl-, alkyl-, halo- or alkoxy-substituted derivatives thereof, wherein halo is chloro or fluoro and alkyl and alkoxy are of 1 to 3 carbon atoms;
  (b) halopyridinyl;
  (c) —$SO_2R_6$, wherein $R_6$ is dialkylamino, alkyl, alkoxy, phenyl, alkylphenyl, halophenyl, alkoxyphenyl, or trifluoromethylphenyl, in which alkoxy, alkyl and halo are defined as above; or the pharmacologically acceptable acid addition salts thereof.

10. The composition according to claim 8 wherein the compound used in effective non-toxic amount is that of formula IIIC

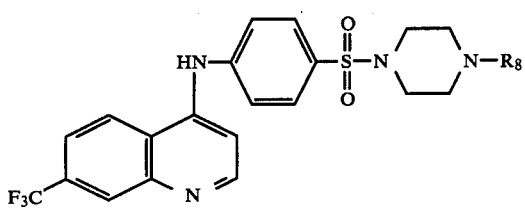

wherein R$_8$ is pyrimidinyl or pyrimidyl substituted with one or two trifluoromethyl, alkyl, alkoxy, or halo groups, in which alkyl and alkoxy are each of one to three carbon atoms, inclusive, and halo is fluoro or chloro; or the pharmacologically acceptable acid addition salts thereof.

11. A method of obtaining antihypertensive effects in a mammal which consists essentially of administering systemically to the mammal a pharmaceutical dosage unit form supplying an effective non-toxic amount, for antihypertensive effects, of a compound of the formula III

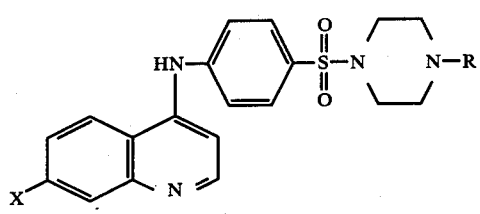

wherein X is chloro or trifluoromethyl; wherein R is
(a) triazinyl;
(b) pyrazinyl;
(c) pyrimidinyl;
(d) triazinyl, pyrazinyl, or pyrimidinyl substituted by one or two trifluoromethyl, alkyl, alkoxy, dialkylamino, alkylthio, or halo, wherein halo is fluoro, bromo, or iodo, wherein alkyl is of one to 3 carbon atoms, and wherein alkoxy is of one to 3 carbon atoms;
(e) halopyridinyl of 1 to 4 halo atoms;
(f) halopyridinyl of less than 4 halo atoms substituted by one or two trifluoromethyl, alkyl, alkoxy, dialkylamino, or alkylthio;
(g)

wherein R$_1$ is phenyl, phenyl substituted with one or two halo, alkoxy, alkyl, trifluoromethylphenyl, or alkylphenyl, wherein alkyl, alkoxy and halo are as defined above; or
(h) —SO$_2$R$_2$, wherein R$_2$ is dialkylamino, phenyl substituted with one or two halo, alkyl, alkoxy, or trifluoromethylphenyl, wherein alkyl, alkoxy, and halo are as defined above; or the pharmacologically acceptable acid addition salts thereof.

12. The method according to claim 11 wherein the compound is of the formula IIIA

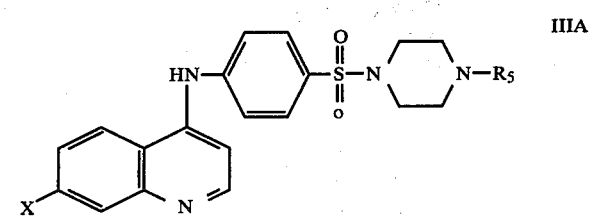

wherein X is chloro or trifluoromethyl; wherein R$_5$ is
(a) pyrimidinyl or the trifluoromethyl-, alkyl-, halo- or alkoxy-substituted derivatives thereof, wherein halo is chloro or fluoro and alkyl and alkoxy are of 1 to 3 carbon atoms;
(b) halopyridinyl;
(c) —SO$_2$R$_6$, wherein R$_6$ is dialkylamino, alkyl, alkoxy, phenyl, alkylphenyl, halophenyl, alkoxyphenyl, or trifluoromethylphenyl, in which alkoxy, alkyl and halo are defined as above; or the pharmacologically acceptable acid addition salts thereof.

13. The method according to claim 12 wherein the compound is of the formula IIIC

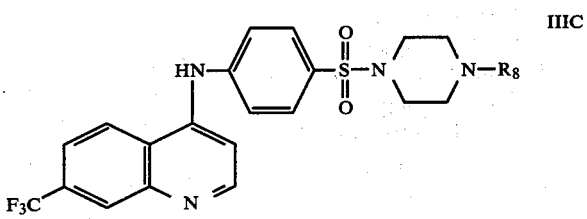

wherein R$_8$ is pyrimidinyl or pyrimidyl substituted with one or two trifluoromethyl, alkyl, alkoxy, or halo groups, in which alkyl and alkoxy are each of one to three carbon atoms, inclusive, and halo is fluoro or chloro; or the pharmacologically acceptable acid addition salts thereof.

* * * * *

UNITED STATES PATENT OFFICE
CERTIFICATE OF CORRECTION

Patent No. 4,159,331                    Dated 26 June 1979

Inventor(s) John M. McCall

It is certified that error appears in the above-identified patent and that said Letters Patent are hereby corrected as shown below:

Column 10, line 20, "[4-quinolinyl]amino]" should read -- 4-quinolinyl]-amino] --; line 21, "246.5°-148.5° C" should read -- 146.5°-148.5° C --;

Column 13, line 44, "sulfonyl]1-4-[[4-[[7-" should read -- sulfonyl]-4-[[4-[[7- --;

Column 14, line 21, "-4-[[-chloro-4-quinolinyl]" should read -- -4-[[4-[[7-chloro-4-quinolinyl] --;

Column 15, line 30, "1-[[4-[7-trifluoromethyl-" should read -- [-[[4-[(7-trifluoromethyl- --;

Column 17, line 19, "-4-[[7-chloro-4-" should read -- -4-[[4-[[7-chloro-4- --;

Column 28, line 42, "or iodo," should read -- or chloro, --; line 57, "$R_1$ is phenyl," should read -- $R_1$ is alkylphenylsulfonyl, phenyl, --; line 58-59, "trifluoromethylphenyl, or alkylphenyl," should read -- or trifluoromethyl, --; line 61-62, "phenyl, substituted with" should read -- phenyl, phenyl substituted with --; line 64, "trifluoromethylphenyl," should read -- trifluoromethyl, --;

Column 29, line 19-20, "$R_6$ is dialkylamino, alkyl, alkoxy, phenyl," should read -- $R_6$ is dialkylamino, phenyl, --

Column 30, line 19, "or iodo," should read -- or chloro, --; line 33, "trifluoromethylphenyl," should read -- trifluoromethyl, --; line 36, "$R_2$ is dialkylamino, phenyl substituted with" should read -- $R_2$ is dialkylamino, phenyl, phenyl substituted with --; line 38, "trifluoromethylphenyl," should read -- trifluoromethyl, --; line 61-62, "$R_6$ is dialkylamino, alkyl, alkoxy, phenyl," should read -- $R_6$ is dialkylamino, phenyl, --;

UNITED STATES PATENT OFFICE

CERTIFICATE OF CORRECTION

Patent No. 4,159,331  Dated 26 June 1979

Inventor(s) John M. McCall

It is certified that error appears in the above-identified patent and that said Letters Patent are hereby corrected as shown below:

Column 31, line 47, "or iodo," should read -- or chloro, --;
Column 32, line 7, "trifluoromethylphenyl, or alkylphenyl," should read -- trifluoromethyl, or alkylphenylsulfonyl, --; line 12, "trifluoromethylphenyl," should read -- trifluoromethyl, --; line 33-34, "$R_6$ is dialkylamino, alkyl, alkoxy, phenyl," should read -- $R_6$ is dialkylamino, phenyl, --.

Signed and Sealed this

Twentieth Day of October 1981

[SEAL]

Attest:

GERALD J. MOSSINGHOFF

Attesting Officer   Commissioner of Patents and Trademarks